US012721625B2

(12) United States Patent
Moubarak et al.

(10) Patent No.: US 12,721,625 B2
(45) Date of Patent: Sep. 1, 2026

(54) INDIRECT END OF CUTLINE DETECTION ON AN ENDOCUTTER WHICH ELIMINATES NEED FOR TOOL CHARACTERIZATION FOR COMPLETION THEREOF

(71) Applicant: Cilag GmbH International, Zug (CH)

(72) Inventors: Paul Moubarak, West Chester, OH (US); Joseph Thomas Mozloom, Jr., Cincinnati, OH (US); Christopher M. Korte, North Bend, OH (US); Jeffrey Franklin, Liberty Township, OH (US)

(73) Assignee: Cilag GmbH International, Zug (CH)

( * ) Notice: Subject to any disclaimer, the term of this patent is extended or adjusted under 35 U.S.C. 154(b) by 186 days.

(21) Appl. No.: 18/608,012

(22) Filed: Mar. 18, 2024

(65) Prior Publication Data

US 2025/0288292 A1 Sep. 18, 2025

(51) Int. Cl.

| | |
|---|---|
| ***A61B 17/072*** | (2006.01) |
| ***A61B 17/068*** | (2006.01) |
| ***A61B 34/32*** | (2016.01) |
| ***A61B 90/00*** | (2016.01) |
| *A61B 17/00* | (2006.01) |

(52) U.S. Cl.

CPC .... *A61B 17/07207* (2013.01); *A61B 17/0684* (2013.01); *A61B 34/32* (2016.02); *A61B 90/06* (2016.02); *A61B 2017/00022* (2013.01); *A61B 2017/00172* (2013.01); *A61B 2017/07271* (2013.01); *A61B 2090/064* (2016.02)

(58) Field of Classification Search

CPC .................................................... A61B 17/072

See application file for complete search history.

(56) References Cited

U.S. PATENT DOCUMENTS

| | | | |
|---|---|---|---|
| 8,210,411 B2 | 7/2012 | Yates et al. | |
| 9,186,142 B2 | 11/2015 | Fanelli et al. | |
| 9,421,014 B2 | 8/2016 | Ingmanson | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 10,092,292 B2 | 10/2018 | Boudreaux et al. | |
| 10,182,813 B2 | 1/2019 | Leimbach et al. | |
| 10,201,347 B2 | 2/2019 | Ingmanson | |
| 10,881,396 B2 * | 1/2021 | Shelton, IV | A61B 17/068 |
| 10,973,516 B2 * | 4/2021 | Shelton, IV | A61B 34/30 |
| 11,090,046 B2 * | 8/2021 | Shelton, IV | A61B 17/0686 |
| 11,141,152 B2 | 10/2021 | Ingmanson | |
| 11,304,697 B2 | 4/2022 | Fanelli et al. | |

(Continued)

OTHER PUBLICATIONS

Extended European Search Report in European Patent Application No. 25164571, dated Jul. 25, 2025, 9 pages.

(Continued)

*Primary Examiner* — Gloria R Weeks

(74) *Attorney, Agent, or Firm* — Lempia Summerfield Katz LLC

(57) ABSTRACT

A surgical stapler instrument drive system which indirectly maximizes the allowed/allotted cutline length of a staple cartridge, and associated staple deployment, with a reduced excess cutting force at the end thereof.

25 Claims, 19 Drawing Sheets

(56) References Cited

U.S. PATENT DOCUMENTS

| | | | | |
|---|---|---|---|---|
| 11,317,912 | B2 | 5/2022 | Jenkins et al. | |
| 11,439,391 | B2 | 9/2022 | Bruns et al. | |
| 11,871,925 | B2 | 1/2024 | Hall | |
| 12,004,745 | B2 * | 6/2024 | Shelton, IV | A61B 17/2833 |
| 2014/0263541 | A1 * | 9/2014 | Leimbach | A61B 17/0686 227/175.2 |
| 2018/0168651 | A1 * | 6/2018 | Shelton, IV | A61B 17/0682 |
| 2018/0360447 | A1 * | 12/2018 | Shelton, IV | A61B 17/0686 |
| 2018/0360449 | A1 * | 12/2018 | Shelton, IV | A61B 17/0686 |
| 2019/0343514 | A1 * | 11/2019 | Shelton, IV | A61B 17/07207 |
| 2021/0085316 | A1 * | 3/2021 | Harris | G16H 40/63 |
| 2022/0000478 | A1 * | 1/2022 | Shelton, IV | A61B 17/068 |
| 2022/0218340 | A1 * | 7/2022 | Harris | G16H 20/40 |
| 2023/0051271 | A1 * | 2/2023 | Shelton, IV | A61B 17/07207 |
| 2023/0108648 | A1 * | 4/2023 | Shelton, IV | G16H 40/63 227/180.1 |

OTHER PUBLICATIONS

Chiradeep Basumallick, "What is Fuzzy Logic? Definition, Working, Pros and Cons", Spiceworks, https://www.spiceworks.com/tech/devops/articles/fuzzy-logic/, Dec. 9, 2022.

Gordon Scott, "Fuzzy Logic: Definition, Meaning, Examples, and History", Investopedia, https://www.investopedia.com/terms/f/fuzzy-logic.asp, Apr. 4, 2023.

* cited by examiner

Handle 20 or Robot

INDIRECT END OF CUTLINE DETECTION ON AN ENDOCUTTER WHICH ELIMINATES NEED FOR TOOL CHARACTERIZATION FOR COMPLETION THEREOF

BACKGROUND

In some settings, endoscopic surgical instruments may be preferred over traditional open surgical devices to minimize the size of the surgical incision as well as reduce post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter (which may combine a grasper, cutter and stapler), grasper, cutter, stapler, clip applier, access device, drug/gene therapy delivery device, energy delivery device using ultrasound, RF, laser, etc.). Endoscopic surgical instruments may include a shaft that extends proximally from the end effector to a handle (or robot attachment) portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected over one or more degrees of freedom, e.g., relative to the longitudinal axis of the shaft.

Examples of endoscopic surgical instruments include surgical staplers. Some such staplers, which may also be referred to as endocutters, are operable to clamp down on layers of tissue, cut through the clamped layers of tissue, and drive staples through the layers of tissue to substantially seal the severed layers of tissue together near the severed ends of the tissue layers. In such instruments, the knife which performs the cutting is further coupled with, or otherwise drives/pushes, either directly or indirectly, a sled which deploys the staples such that the two move together to substantially simultaneously transect and staple the clamped tissue. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path.

Each cartridge physically defines or is otherwise capable of transecting/cutting or making a cutline of a certain allowed/allotted maximum length, referred to as the cutline length, and introducing two or more lines of staples of the same or varying length, referred to as staple lines, running parallel to, and with at least one staple line on either side of, the cutline. As shown in FIG. 9, often the cartridge defines the maximum allowed nominal length of the staple lines to exceed the maximum allowed length of the cutline, both distally and proximally (not shown), by a margin, e.g. 1-5 mm, to improve hemostasis of the transected tissue(s). As the knife, which performs the cutting, and the sled, which deploys the staples, as was described above, often move together, the length of the deployed staple line(s) may be a function of the length of the cutline. Furthermore, as the sled acts to effectively push each staple up and out into the tissue as the sled advances, should the sled not reach the end of the cartridge, the remaining staples may be partially but not completely deployed. Therefore, the maximum cutline length must typically be achieved so as to fully deploy all of the staples from the cartridge.

It is therefore desirable that, when firing the stapler, the maximum allowed cutline length, and therefore, the maximum allowed lengths of the staple line(s) be obtained, ensuring a the clamped tissue is appropriately transected and the staples are properly deployed.

The features of the present disclosure seek to enable an endocutter to maximize the allowed/allotted cutline length of a staple cartridge, and associated staple deployment. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
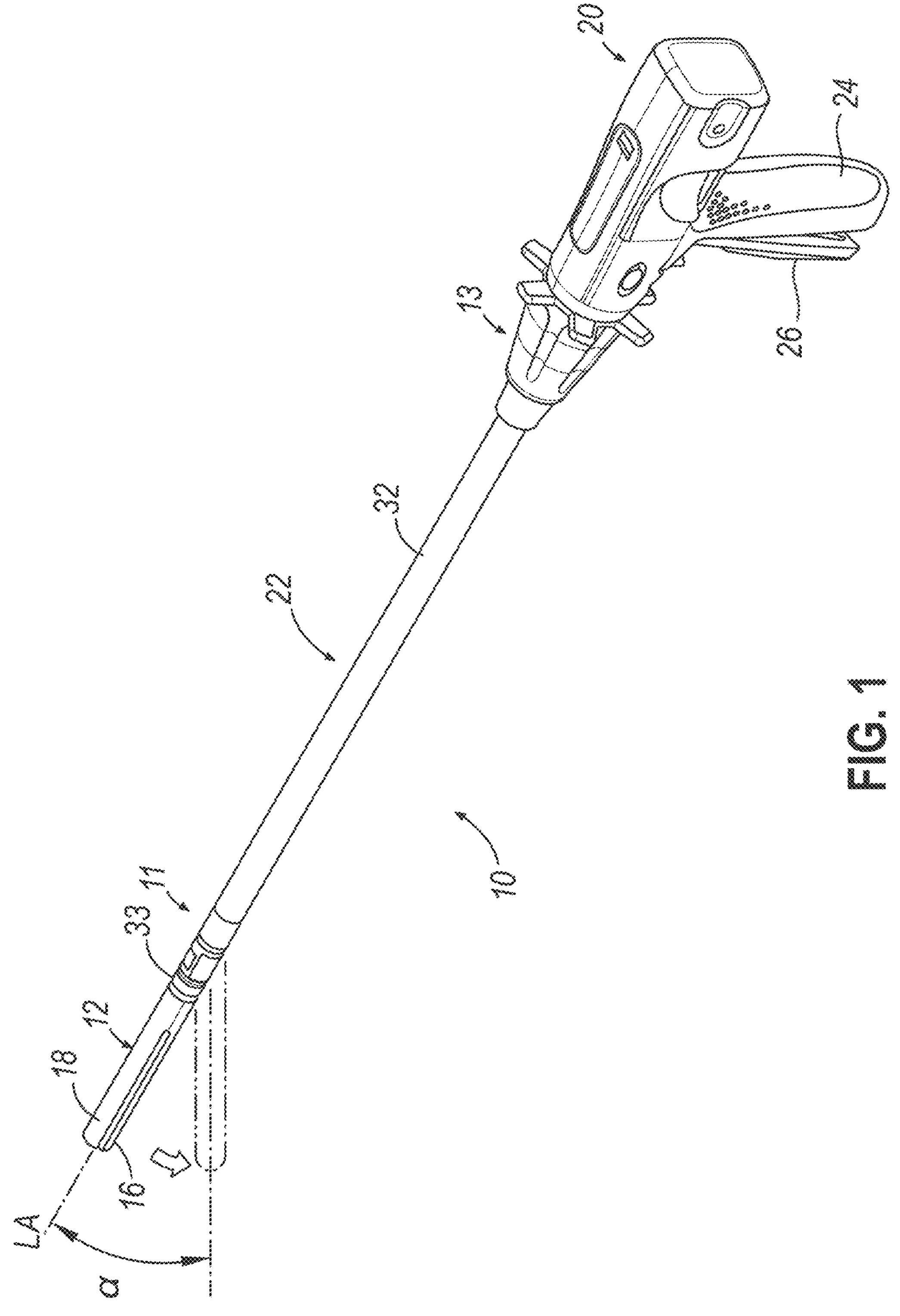
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected in one or more directions/degrees of freedom from the longitudinal axis (LA) of shaft 22 at a desired angle ($\alpha$), referred to as a "pose." End effector 12 of the present example includes a lower jaw 16 (also referred to herein as a cartridge jaw) that includes a staple cartridge 37, and an upper jaw in the form of a pivotable anvil jaw 18. As described elsewhere herein, in robotic application, the handle portion 20 may be replaced with a suitable adapter for coupling the instrument 10 with a robotic arm.

Unless otherwise described, the term "pivot" (and variations thereof) as used herein encompasses but is not necessarily limited to pivotal movement about a fixed axis. For instance, in some versions, anvil jaw 18 may pivot about an axis that is defined by a pin (or similar feature) that slidably translates along an elongate slot or channel as anvil jaw 18 moves toward lower jaw 16. Such translation may occur before, during, or after the pivotal motion. It should therefore be understood that such combinations of pivotal and translational movement are encompassed by the term "pivot" and variations thereof as used herein.

Handle portion 20 includes a pistol grip 24 and a closure trigger 26. Closure trigger 26 is pivotable toward pistol grip 24 to cause clamping, or closing, of anvil jaw 18 toward lower jaw 16 of end effector 12. Such closing of anvil jaw 18 may be provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33.

Figure 2:
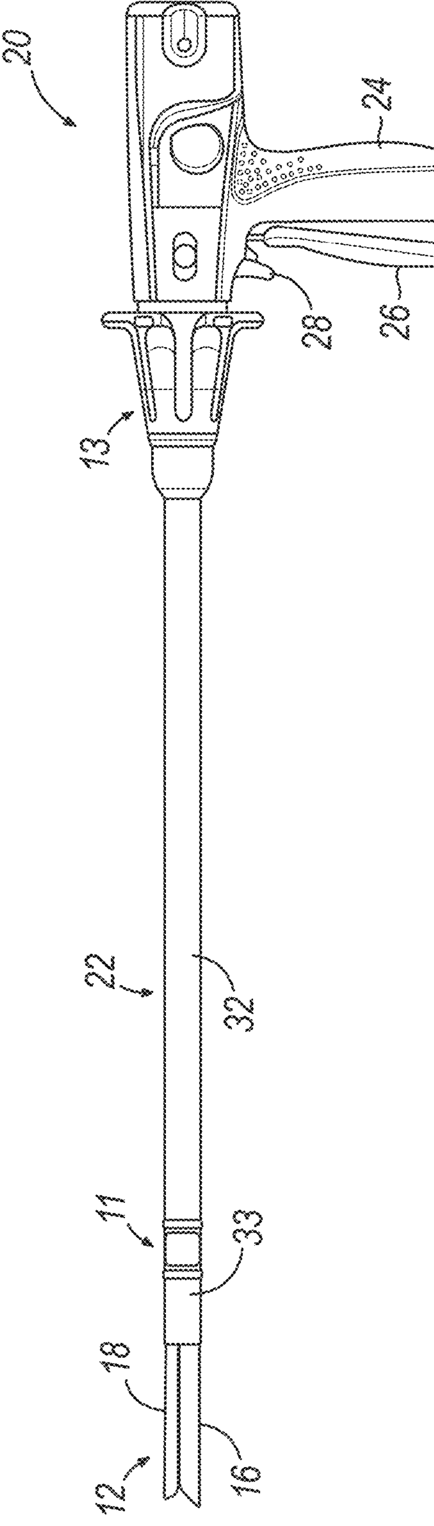
FIG. 2 depicts a side view of the instrument of FIG. 1.

As shown in FIG. 2, handle portion 20 also includes a firing trigger 28. The instrument 10 further includes a drive train, or driver, comprising one or more driving and/or driven components, including an elongate drive member (not shown), such as a shaft, rod or beam, which longitudinally extends through shaft 22, that communicate/translate a longitudinal or rotational firing motion from handle portion 20, e.g., from a trigger and/or motor included therein, to a firing beam 14 of the end effector 12. In some articulated instruments 10 which enable the end effector 12 to be posed in different positions relative to the shaft 22, the drive train may further include one or more flexible components/connectors which pass through the articulation joint 11 and enable conveyance/translation of the firing motion therethrough regardless of the pose thereof.

In a manually actuated instrument 10, the firing motion is produced via actuation of the firing trigger 28 which longitudinally advances/displaces the drive train, i.e., a proximal end of the elongate drive member, and, thereby, advances/displaces the firing beam 14. In a motorized instrument, wherein the motor (not shown) may be located in the handle or the robot, the firing motion is produced via operation of the motor which is coupled with the drive train and which may be activated in response to actuation of the firing trigger 28 or other input actuated by the user, which is translated, rotationally and/or linearly/longitudinally via the drive train and thereby advances/displaces the firing beam 14.

This distal translation of firing beam 14 causes the stapling and severing of clamped tissue in end effector 12, as will be described in greater detail below.

As shown in FIGS. 3-6, end effector 12 employs a firing beam 14 that includes a transversely oriented upper pin 38, a firing beam cap 44, a transversely oriented middle pin 46, and a distally presented knife/cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44. As will be described, as the knife/cutting edge 48 advances through the cartridge slot 49, a lower portion of the cutting edge 48 engages, directly or indirectly, the sled 41 to push the sled 41 forward. As used herein, cutting edge 48 refers to the entire cutting edge 48 assembly including the sharpened edge which moves through the cartridge slot 49 and actually engages/cuts the tissue, and the portions above and below which engage the slots 42, 45, in the upper and lower jaws 16, 18, which guide the cutting edge 48 as it advances distally and retracts proximally, as well as the portion which engages and pushes, directly or indirectly, the sled 41. In some embodiments, the cutting edge 48 directly engages/pushes the sled 41. In alternative embodiments, one or more intermediate driving components may be implemented between the sled 41 and the portion of the cutting edge 48 which engages and pushes the sled 41. In this implementation, the cutting edge 48 indirectly engages/pushes the sled 41, i.e., the cutting edge 48 engages/pushes the one or more intermediate driving components which in-turn engages/pushes the sled 41.

Figure 3:
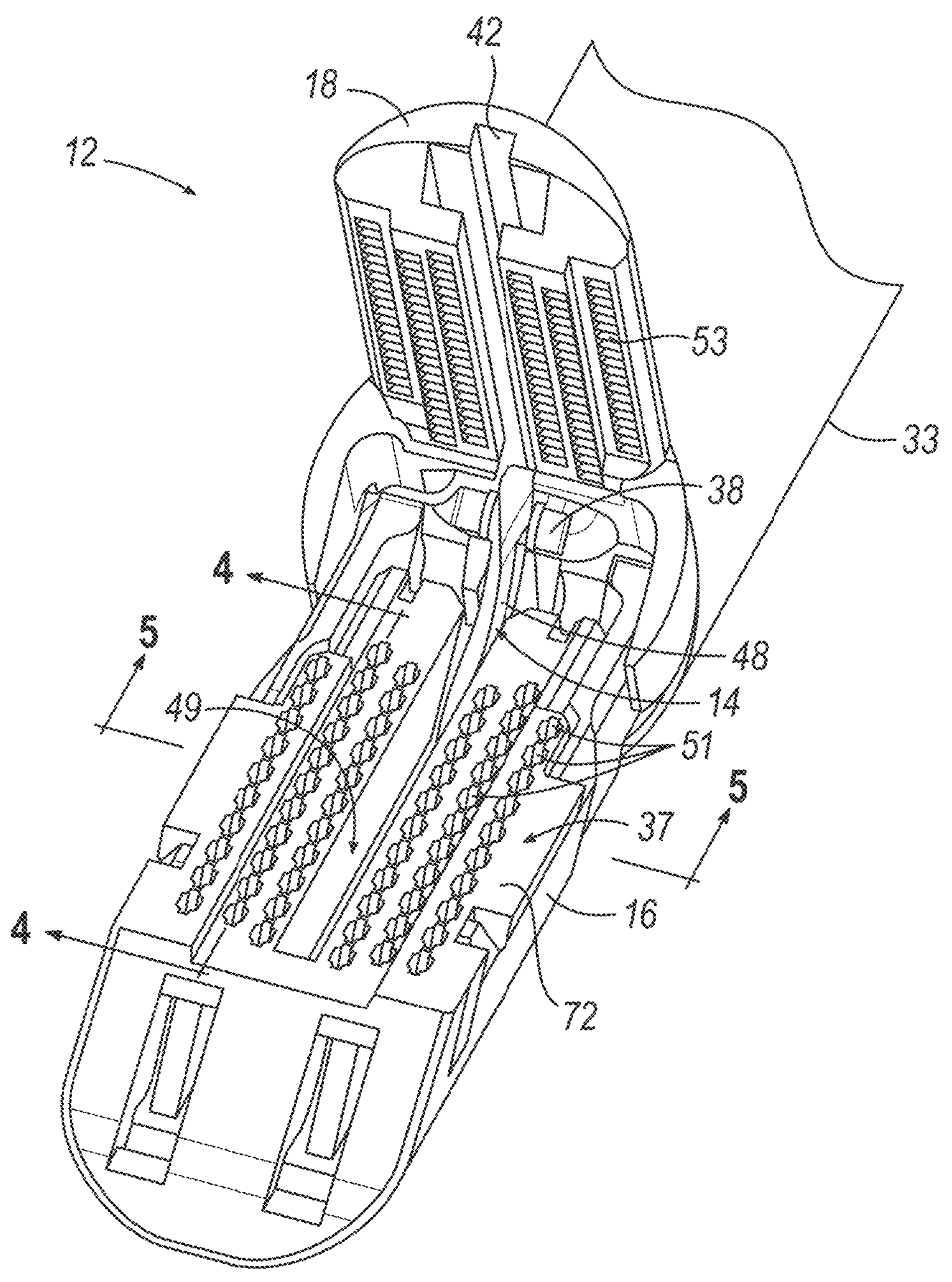
FIG. 3 depicts a perspective view of an opened end effector of the instrument of FIG. 1.
Figure 4A:
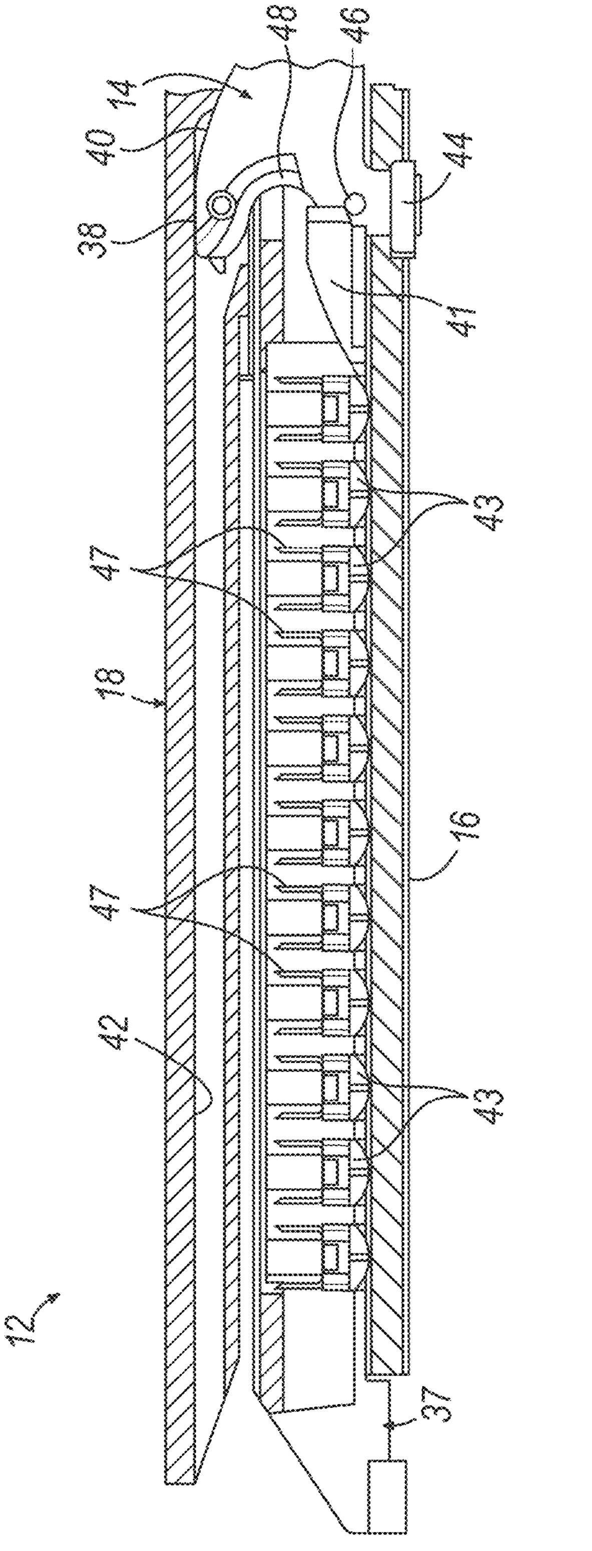
FIG. 4A depicts a side cross-sectional view of the end effector of FIG. 3, taken along line 4-4 of FIG. 3, with the firing beam in a proximal position.
Figure 4B:
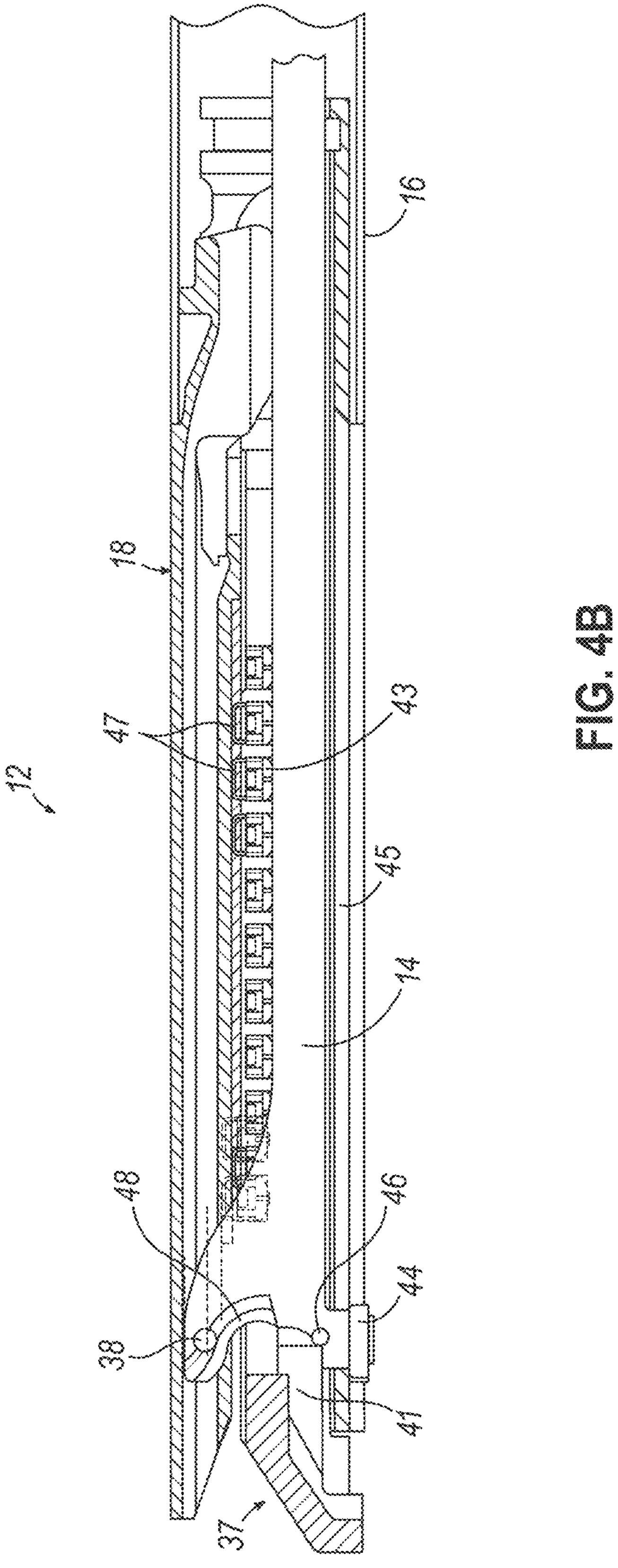
FIG. 4B depicts a side cross-sectional view of the end effector of FIG. 3, taken along line 4-4 of FIG. 3, with the firing beam in a distal position.
Figure 5:
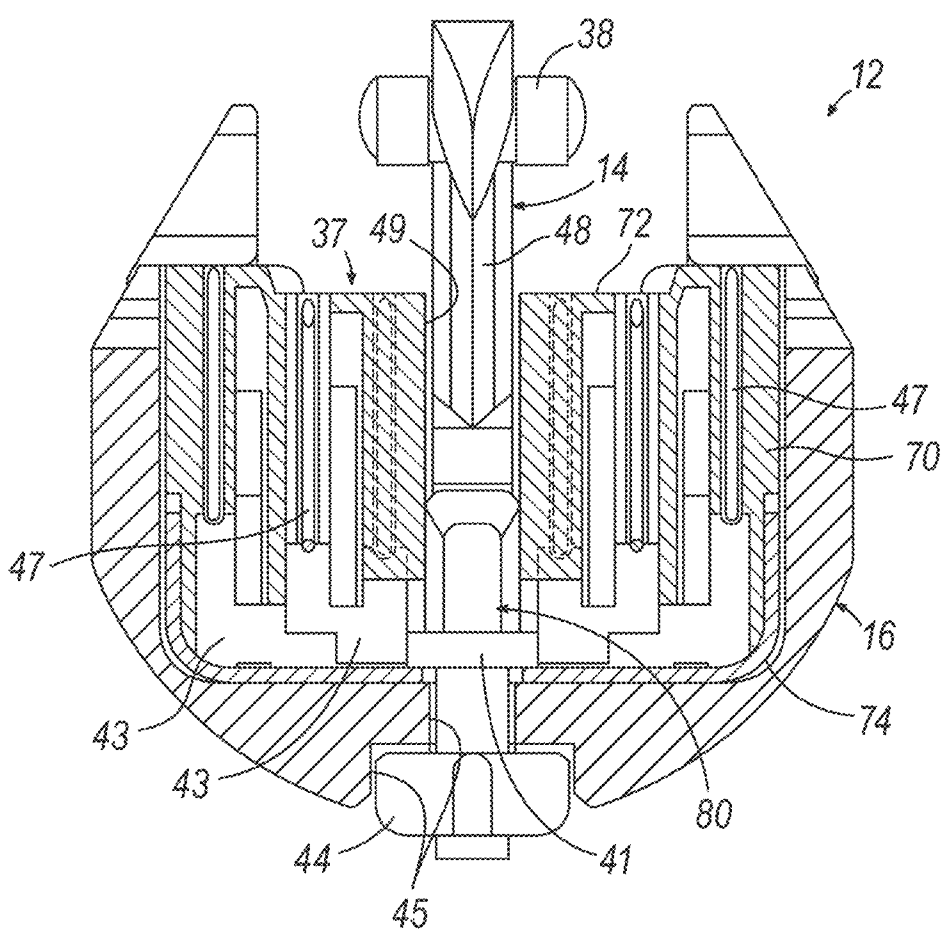
FIG. 5 depicts an end cross-sectional view of the end effector of FIG. 3, taken along line 5-5 of FIG. 3.
Figure 6:
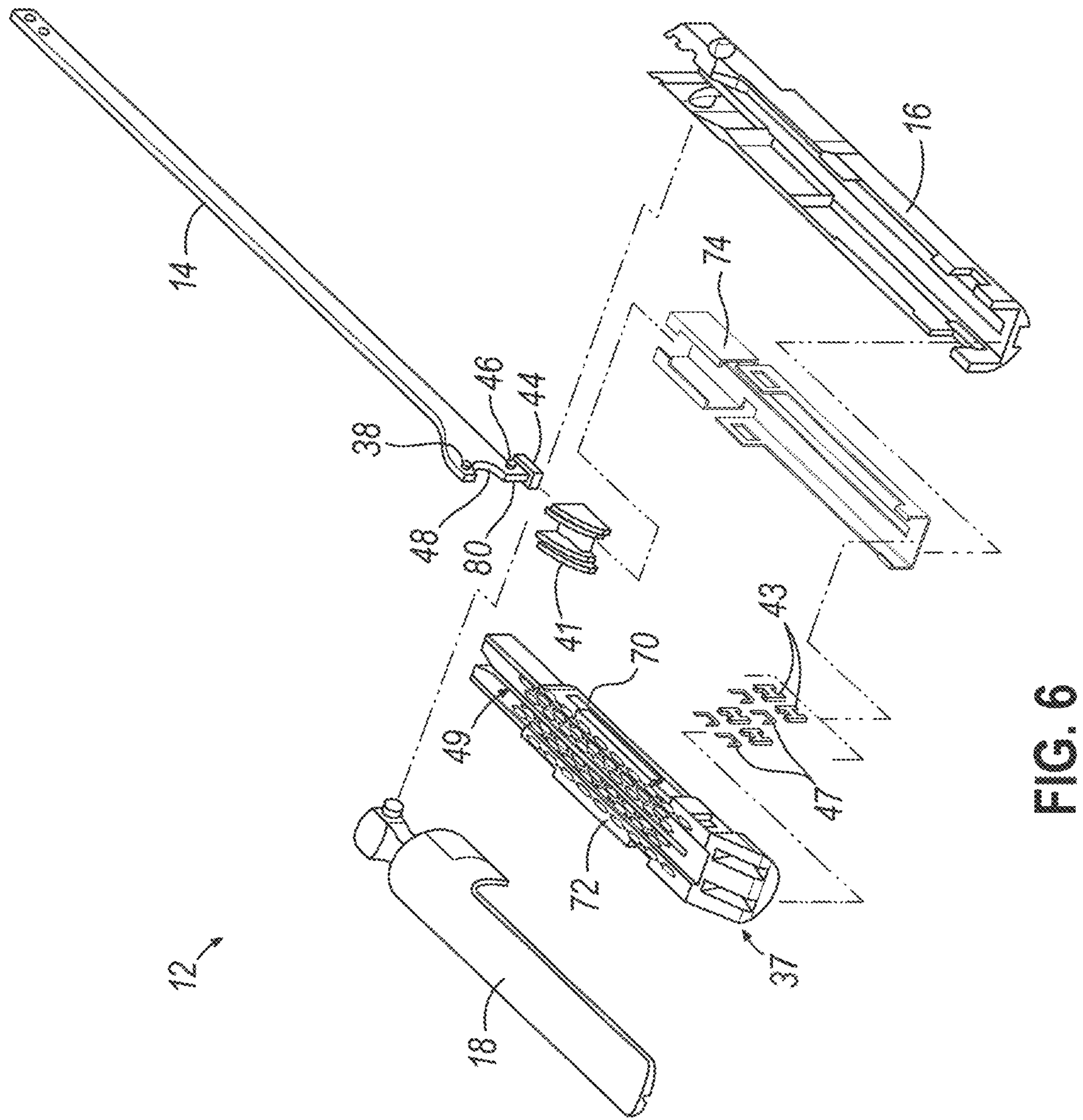
FIG. 6 depicts an exploded perspective view of the end effector of FIG. 3.

FIG. 3 shows firing beam 14 of the present example proximally positioned and anvil jaw 18 pivoted to an open configuration, allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80 (shown in FIG. 5) located at distal end of firing beam 14 pushes wedge sled 41 distally as firing beam 14 is advanced distally through staple cartridge 37 when firing trigger 28, or otherwise the motor, is actuated. During such firing, cutting edge 48 of firing beam 14 enters vertical slot 49 of staple cartridge 37, severing tissue clamped between staple cartridge 37 and anvil jaw 18. As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS. 4A-4B but are shown in FIG. 3. Anvil jaw 18 is intentionally omitted from the view in FIG. 5.

Figure 7:
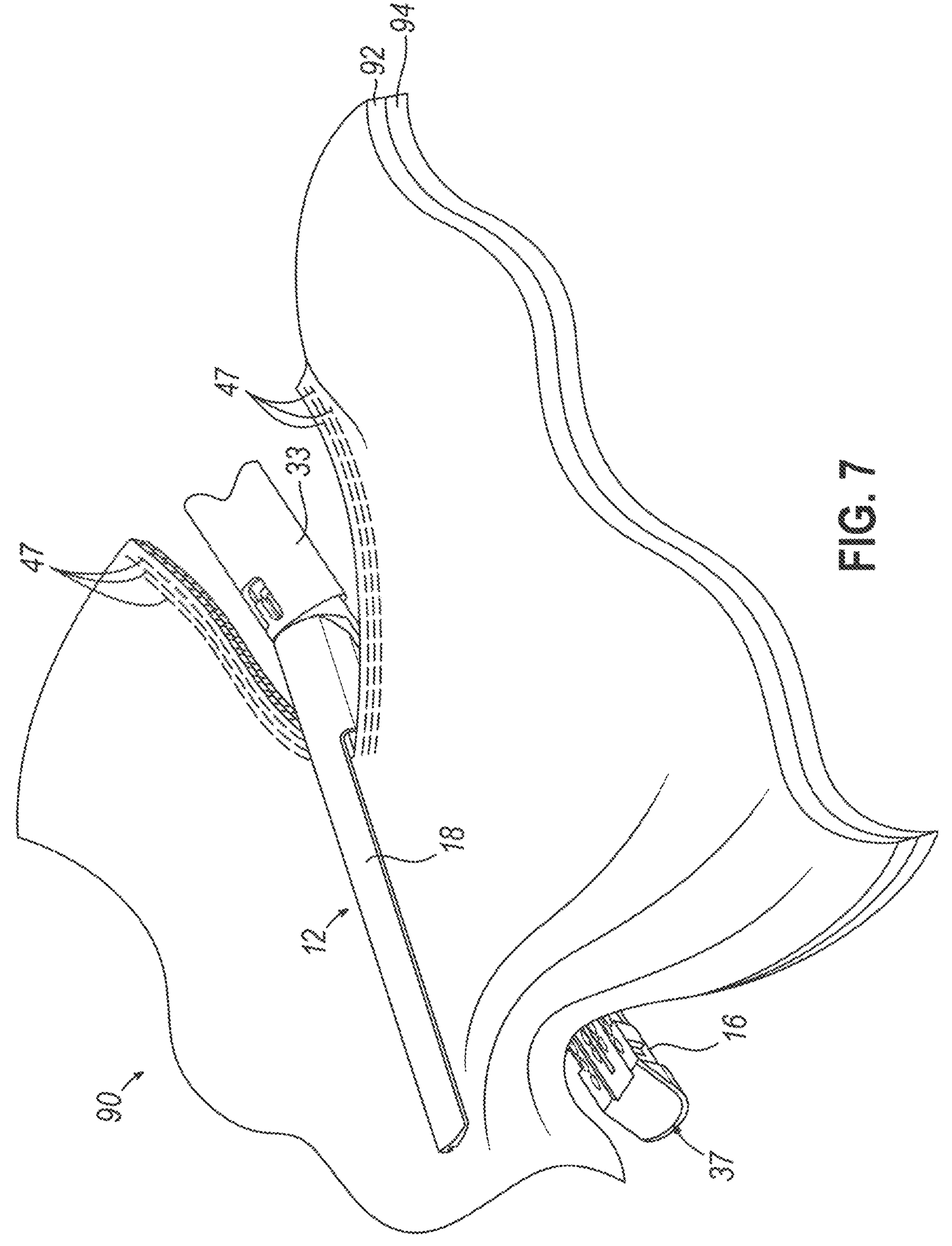
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 (staple lines) through tissue 90 on each side of the cut line produced by cutting edge 48. After the first firing stroke is complete, end effector 12 is withdrawn from the patient, before or after retracting the cutting edge 48, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 11,871,925, entitled "Surgical Instruments with Dual Spherical Articulation Joint Arrangements" issued Jan. 16, 2024.

In some instances, it may be desirable to provide the user with better visualization of end effector 12. In particular, as end effector 12 is inserted into a surgical site, the user may rotate shaft 22 of instrument 10 during the procedure. As a result, end effector 12 also rotates. As end effector 12 rotates, it may be desirable for the user to have visual access to the surgical site. For instance, the user may wish to see the interface or contact between tissue 90 and end effector 12. Since end effector 12 may be rotated about the longitudinal axis (LA) relative to handle portion 20, the user may view the surgical site such that lower jaw 16 of end effector is visible rather than anvil jaw 18. Alternatively, end effector 12 could be rotated such that when the user views end effector 12, anvil jaw 18 is visible by the user. It may be desirable to provide visibility of the surgical site for the user beyond what is possible in instrument 10 of FIG. 1.

For instance, in the case of some surgical procedures where fluid carrying vessels are transected and stapled, it may be desirable to have visual confirmation that anvil jaw 18 and lower jaw 16 completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector 12 has been positioned properly within the surgical site for anvil jaw 18 and lower jaw 16 to fully clamp the vessel. One potential way of monitoring the surgical site may include improving visualization of the area adjacent to the distal tip of lower jaw 16 and anvil jaw 18. Furthermore, not only visualization of the distal end of end effector 12 may be desirable, but also it may be desirable to construct end effector 12 such that the distal end of anvil jaw 18 is configured to urge tissue (e.g., a large vessel) proximally into the space between anvil jaw 18 and lower jaw 16 as anvil jaw 18 closes toward lower jaw 16.

In addition to the foregoing, end effector 12 and versions of instrument 10 incorporating end effector 12 may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector 212 will be described in greater detail below.

Figure 8:
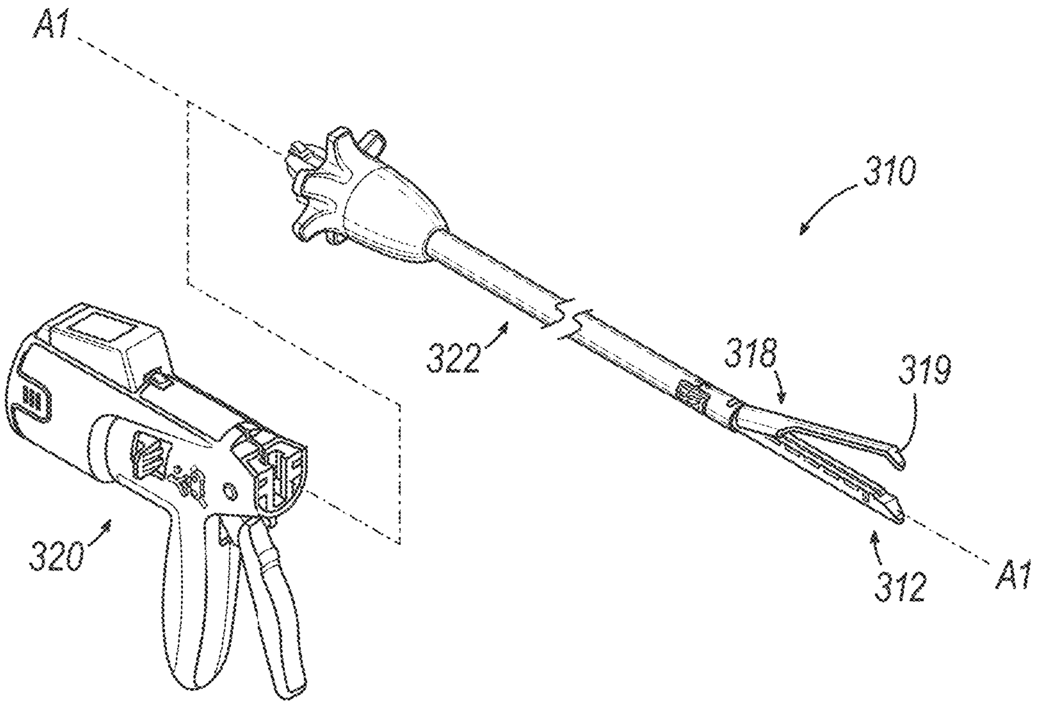
FIG. 8 depicts a perspective view of an example of a surgical stapling instrument having an end effector with a curved elastically deformable tip section.

FIG. 8 shows another example of an instrument 310 configured as a surgical stapler. Instrument 310 includes a handle portion 320 and a shaft 322. Instrument 310 has a modular configuration such that shaft 322 is selectively removable from, and attachable to, handle portion 320. Instrument 310 is configured similarly to instrument 10 such that the operability and use of instrument 310 is the same as described above for instrument 10 with the added feature of instrument 310 being a modular configuration. With its modular configuration, instrument 310 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 310 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 310 with a modular configuration will be apparent to those of ordinary skill in the art in view of the teachings herein. Moreover, it will be understood by those of ordinary skill in the art in view of the teachings herein, that instrument 10 may be modified to incorporate a modular configuration as shown and described with respect to instrument 310 or other instruments incorporated by reference herein. The instrument 310 further includes a distal tip 319, which may be bendable (moving when force is applied and returning to its original position when no force is applied), malleable (moving to a position when force is applied and remaining in that position when no force is applied), or discretely articulated to one or more discrete/low energy positions when force is applied and remaining in that discrete position via a retention mechanism. The tip 319 may provide for not only visualization of the distal end of end effector 12, but also may enable the end effector 12 such that the distal end of anvil jaw 18 can be used to urge tissue (e.g., a large vessel) proximally into the space between anvil jaw 18 and lower jaw 16 as anvil jaw 18 closes toward lower jaw 16.

It will be appreciated that end effector 312 may be used in place of end effector 12 shown in FIG. 1. In some versions, end effector 312 may be integrally formed with shaft 22 or alternatively may be separately formed and then combined. In some versions, end effector 312 may be provided for use in robotic systems. In such robotic systems, modular shaft 322 having end effector 312 may be attachable to a portion of the robotic system for use such that handle portion 320 is replaced by components of the robotic system which provide the mechanism, i.e., motor, to actuate the firing stroke as described above. Still in other examples, end effector 312 may be adapted for use with a robotic system in a manner where end effector 312 connects with the robotic system without necessarily connecting the entire modular shaft 322. In view of the teachings herein, other ways to incorporate an end effector having an angled elastically deformable anvil tip into a user operated or robotic operated instrument will be apparent to those of ordinary skill in the art.

The disclosed embodiments relate to ensuring that the length of the cutline of the stapler/cutter is maximized without having to first characterize the tool, reducing the magnitude of the force applied to complete that cutline.

An algorithm, and implementation thereof, is disclosed that detects end of cutline using proximal cutting edge and firing force information available freely from the control system of the surgical instrument 10, without the need for sensors and/or switches disposed in the end effector 12 to sense when the end of the firing stroke is reached.

Figure 18:
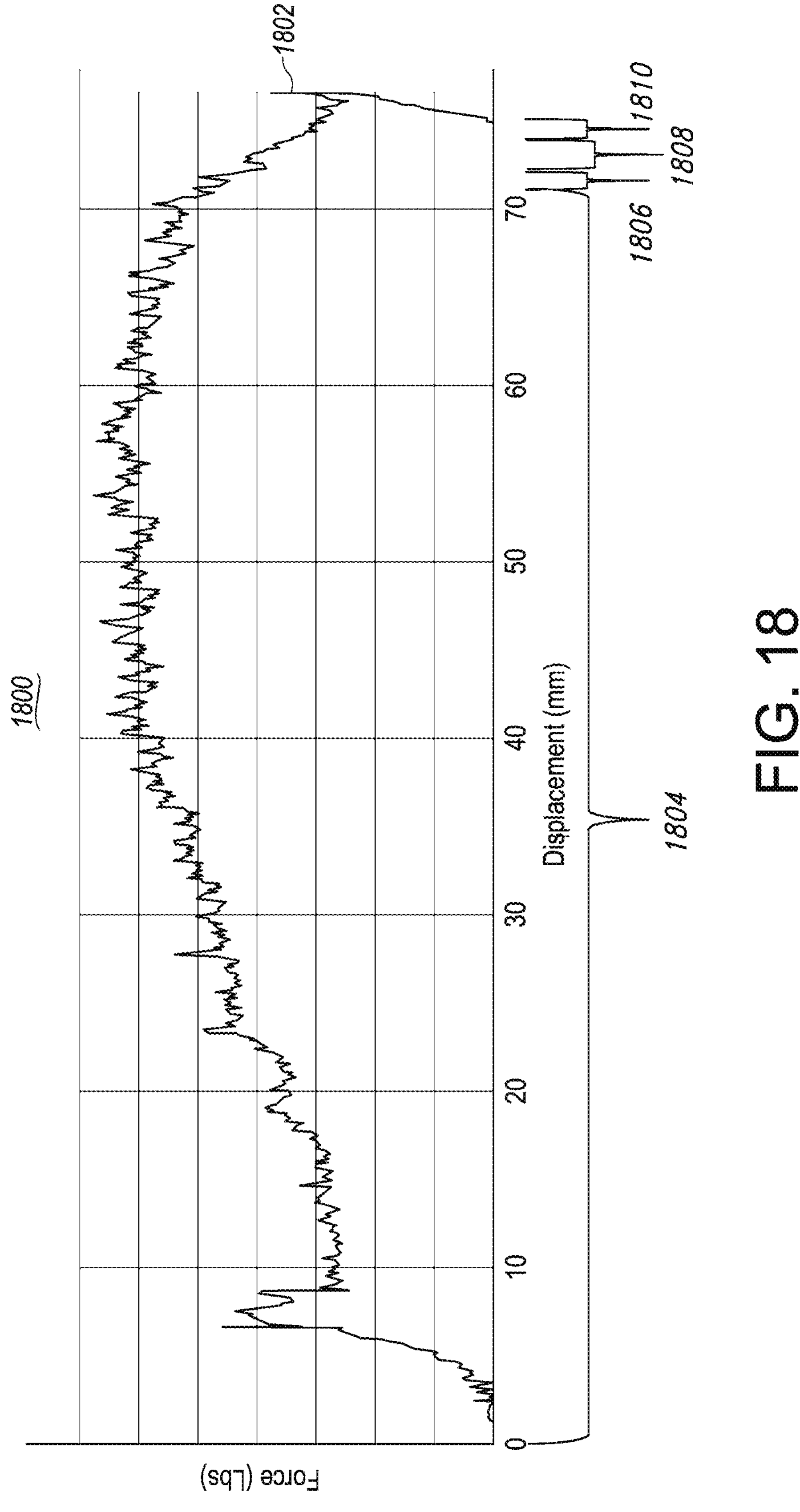
FIG. 18 depicts a graph of example forces applied at the distal end of the drive train during a transection of tissue to attempt to maintain a set displacement rate over the distance displaced thereby according to some embodiments.

In one embodiment, as the cutting edge 48 travels down the slot 49 of the cartridge 37 and approaches a region proximate to the end of cutline 1804, the motor of the surgical instrument 10 decelerates in order not to hit the end of cutline at high speed 1806 and a buffer starts to build up data values representative of the real time force/torque being applied by the motor to maintain the current rate of displacement and the corresponding current position/displacement of the drive train by the motor 1808. The buffer is an array of real time positions of the cutting edge 48 and real time cutting edge 48 forces provided by, for example, the motor's encoder and torque sensor which may then form a graph of force vs displacement distance from which a projected force may be extrapolated as described herein. FIG. 18 depicts a graph 1800 of example forces applied by the motor to attempt to maintain the particular rate of displacement over the displacement distance which may be stored in the buffer array. As the cutting edge 48 gets closer to the end of the cutline 1810, a best-fit function of force and position is performed in real time on the stored array values using either linear, best-fit curve or quadratic fit function, via interpolation and/or smoothing. This gives information on the slope of force vs. position, i.e., how the firing force is trending relative to the cutting edge 48 position and enables a projection of that trending force over subsequent increments of travel, enabling preemptive action prior to or at the end of the cutline as described herein. After that, a projection of, for example, 3 or more discrete horizons into the future is made at every processing loop time using the best-fit function in order to anticipate a cutting edge 48 force into the future using a-priori information. This projection then factors in the cutting edge 48 force that was needed to transect the tissue over the monitored distance based on the properties of that tissue and compliance/losses of the instrument, and projects the cutting edge 48 force anticipated to be needed to complete the cutline through the remaining tissue. As depicted in FIG. 18, if, as the cutting edge 48 advances, the actual cutting edge 48 force 1802, as sensed by the motor, exceeds a threshold, for example, 10% to 20% of the projected force, the algorithm informs the motor that a higher than projected force is detected indicative of reaching the end of the allowed cutline, i.e., pushing the sled into the end of the cartridge or into another physical impediment, and requests a stop. Thereby, accuracy of achieving end of cutline, with different tissue thicknesses and different end-effector poses, is improved with a minimal deviation, e.g., <0.2 mm.

In an alternative embodiment, as the cutting edge 48 travels down the cartridge 37 and approaches the distal end of the cartridge 37 (the region near the end of cutline), the cutting edge's 48 velocity is reduced. The cutting edge's 48 firing forces and position, as determined by the motor control circuit, are sampled, and the change in cutting edge's 48 firing force with respect to its change in position (dF/dx) is calculated. The cutting edge's 48 position and dF/dx are each fed into a fuzzy logic set (for example, one set for position and one set for dF/dx). Those fuzzy logic sets convert the two inputs into six fuzzy-logic membership functions. Fuzzy logic rules, e.g., five rules, combine the outputs of the fuzzy logic membership functions, e.g., six functions. The output of each rule is a value that represents how much the rule wants to continue or stop the movement of the cutting edge 48. The outputs of the fuzzy logic rules are combined yielding a single binary result: continue or stop. If the result is to continue, the cutting edge 48 continues to move, and the firing forces and position are sampled, and sent back through the fuzzy logic cutline algorithm. If the result is to stop, the motor is directed to stop.

More particularly, as was described elsewhere herein, the staple cartridge 37 includes a slot 49 through which the knife/cutting edge 48 of the end effector 12 travels. Generally, this slot 49, along with the cartridge body 37, will define the maximum distance that the cutting edge 48 can travel and therefore the maximum length of the cutline created by the cutting edge 38. Different types of cartridges 37 may enable different cutline lengths and it may be important to ensure that the maximum allowable cutline length is obtained, e.g., to ensure that the tissue is completely transected, etc. In addition, as described herein, as the cutting edge 48 also advances the sled 41, either directly or indirectly, of the cartridge 37 which deploys the staples 47, obtaining the maximum cutline length also ensures that the distal staples 47 are properly and fully deployed and formed, ensuring the maximum staple line length is also achieved.

Figure 9:
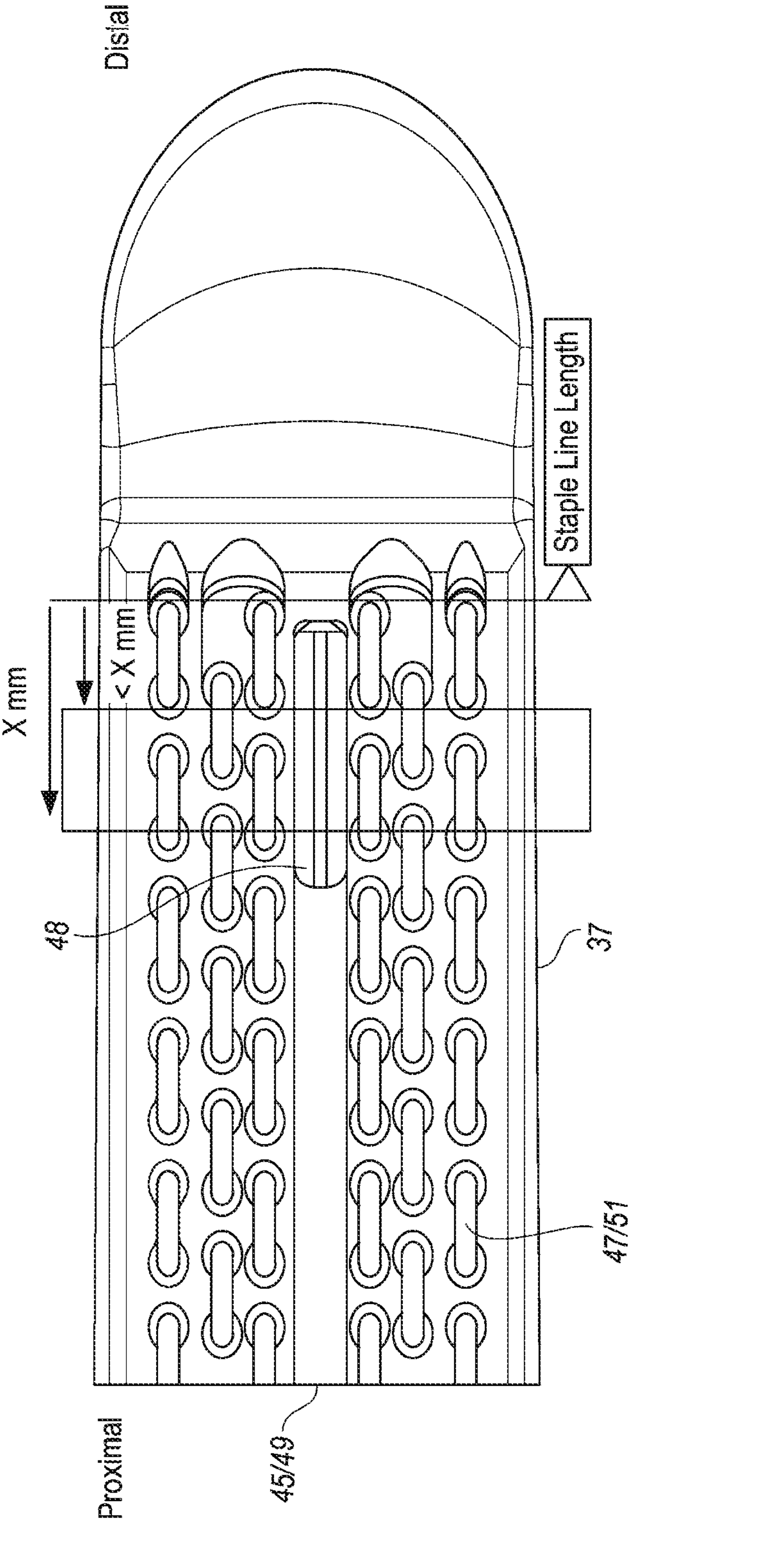
FIG. 9 depicts a top down view of a distal end of an example staple cartridge showing the staple apertures and cutting edge slot and cutting edge.

The maximum cutline length will generally be less than the length of the staple lines created by the cartridge 37 (X as shown, for example, in FIG. 9) when fired. More particularly, to ensure hemostasis of the transected tissue, it may be important that the staple line extend both distally and proximally beyond the cutline by a small margin. As shown in FIG. 9, for example, the maximum length of the cutline may be <X mm, e.g., 2-10 mm, distally shorter than the nominal staple line length X of the six parallel staple lines provided by the depicted cartridge 37. It will be appreciated that different cartridge 37 types may feature shorter or longer cutlines and or staple lines, and/or have fewer or more staple lines, and/or staple lines of differing configurations.

The distance that the cutting edge 48 travels down the slot 49 controls the length of the cutline that is achieved. And as described elsewhere herein, the cutting edge 48 is driven by a remotely located motor, e.g., located in the handle 20 or robot, via a drive mechanism which runs through the shaft 22 and, if present, articulation joint 11, to the end effector 12.

As will be described, the distance by which the motor advances or otherwise displaces the drive mechanism does not always result in the cutting edge 48 advancing/displacing through the cartridge 37 by the same amount, e.g., 1 mm of motor displacement may not result in 1 mm of cutting edge 48 travel and this discrepancy may vary over the length of the cutline, resulting in the cutting edge 48 travelling, for example, 2-3 mm less than the driven distance/displacement.

This may be a result of compliance/elasticity issues with one or more components of the drive mechanism/train which may, for example, absorb, dampen or dissipate at least a portion of the force applied by the motor, such as due to frictional losses or losses due to tolerances in the components, or otherwise yield, deform or compress under the load of the force applied by the motor at the proximal end of the drive mechanism and/or the resistance encountered by the cutting edge 48 at the distal end of the drive mechanism, e.g., due to the thickness or resistance or other properties of the tissue being cut.

In addition, in order to enable articulation of the end effector 12, some components of the drive mechanism may be required to be flexible so as to pass through the articulation joint 11 and remain operable regardless of the pose of the end effector 12. This may add to the compliance in the overall drive mechanism. Further, this added compliance may vary depending upon the pose of the end effector.

Compliance may also be a function of the design of the components, the materials used, number and type of component interconnections/linkages, manufacturing tolerances, wear and tear from use, etc.

It may be suggested that in order to maximize the cutline length, the motor need only advance the drive mechanism, and thereby the cutting edge 48, until the cutting edge 48 cannot be physically advanced any further. However, the motors used in endocutters can deliver a significant amount of force, e.g., in excess of 200 ft/lbs, so as to reliably be able to cut different types of tissue. If one were to simply drive the cutting edge 48 until it impacted with some physical impediment, i.e., over-travelling, such as the end of the cartridge 37 housing, with even a fraction of the available force, the resultant dissipation of the excess force may cause an unexpected movement or vibration of, or noise from, the instrument 10, damage to the instrument 10, such as to the motor or one or more components of the drive mechanism, damage to the cartridge 37, such as a fracture of the cartridge 37 housing (bursting), and/or partial or full de-articulation of the posed end effector 12, i.e., the force of the impact may overcome the force applied by the articulation mechanism, e.g., tension cables, used to hold the end effector 12 in a particular pose causing the end effector 12 to move. Any of these may result in disconcerting user feedback, premature instrument wear or breakage, extension of the cutline to or beyond the staple lines, tissue damage and/or other patient injury.

It may be further be suggested to include a sensor or switch in the end effector 12 which detects when the cutting edge 48 reaches the maximum cutline distance and then causes the motor to stop advancing the drive mechanism. However, the inclusion of sensors and/or switches may complicate the design, manufacturing and/or operation of the instrument 10, e.g., necessitating additional components and wiring to couple those components through the end-effector 12, articulation joint 11, shaft 22, etc. and with a control mechanism which controls the motor. This may result in increased cost as well as increased points of failure, etc.

To minimize such results, other firing mechanisms have utilized an open loop control which required first characterizing, or otherwise calibrating, the firing mechanism so as to determine, for a given pose or other condition of the instrument 10, a relationship between the distance that the motor advances the drive mechanism and the resulting distance that the cutting edge 48 advances. As an open loop control system does not utilize feedback, this initial characterization is important to ensure that cutline distance is maximized but not exceeded.

However, characterizing the firing mechanism before each use may be inconvenient and may fail to produce an accurate indication of the relationship between the distance advanced by the motor and the resultant cutting edge 48 travel distance. For example, variations in compliance caused by manufacturing variations, repeated use of the instrument, pose/configuration of the instrument, characteristics of the tissue being transected, alone or in combination, may affect accuracy.

The disclosed embodiments reach a precise position of the cutting edge 48 at the end of the cutline, e.g., not too far in order to prevent de-articulation or bursting of sled and not too short in order to not cause partially formed staples, regardless of the variance caused by the configuration/poses of the instrument 10, compliance of the components thereof, or the properties of the tissue being cut. The disclosed embodiments do not rely on having to correlate the drive distance, Compliance and actual movement of the cutting edge 48 or on sensors or switches in the end-effector 12, or otherwise characterize the instrument 10, to detect end of cutline.

Figure 10:
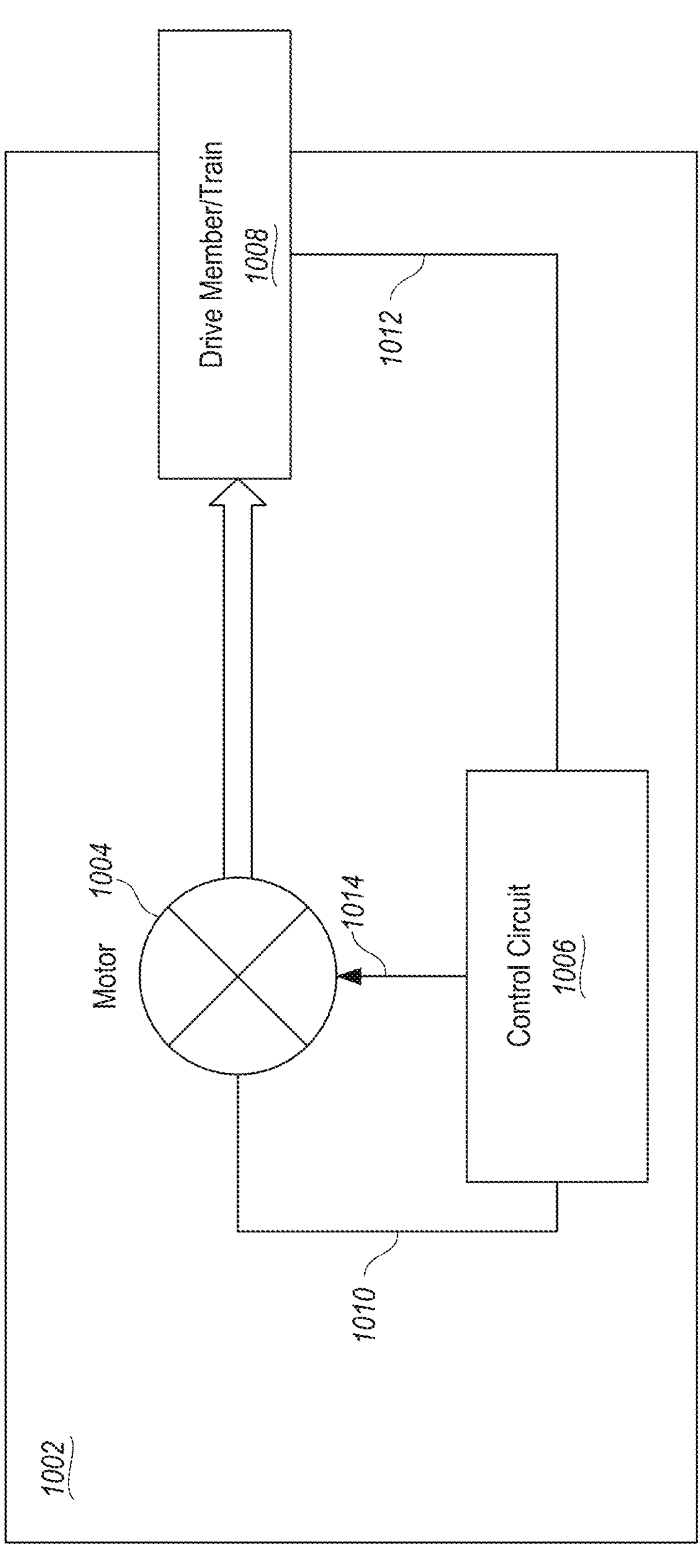
FIG. 10 show a block diagram of system for operating a surgical stapling instrument according some embodiments.

Referring to FIG. 10, there is shown a block diagram of system 1002 for operating a surgical stapling instrument 10 according some embodiments, the surgical stapling instrument 10 comprising: an end effector 12 configured to grasp tissue, the end effector 12 comprising: jaws 16, 18 comprising a cutting edge 48 configured to be displaced a first distance, e.g., a maximum allowed cartridge 37 cutline length, from a proximal end to a distal end of the jaws 16, 18 such that at least a portion of the cutting edge 48 transects tissue grasped by the end effector, the jaws 16, 18 further configured to receive a staple cartridge 37 seatable in one of the jaws 16, 18 and including a sled 41 and staples 47, the sled 41 configured to be displaced a second distance, e.g., a maximum sled travel distance or staple line length, from a proximal end to a distal end of the staple cartridge 37 to deploy the staples 47 into the tissue grasped by the end effector 12 along the transection. As was described elsewhere herein, the second distance may extend both proximally and distally beyond the first distance such that the deployment of the staples both begins before, and extends beyond the transection of the tissue, i.e., the cut line does not extend beyond the staple line, e.g., to promote hemostasis of the transected tissue.

The instrument 10, or otherwise a robot, further comprises a motor 1004 located external to the end effector 12. The motor 1004 may be any suitable motor, electrically powered or otherwise by a power source (not shown) and which may provide for a rotational or linear actuation to displace/advance a driver/drive train 1008 of the instrument 10. The drive train 1008 may comprise multiple linked driving and/or driven components, including the drive member which longitudinally extends through the shaft 22 as was described above, which translate the displacement and force applied by the motor 1004 to the cutting edge 48.

The instrument 10 and/or a robot may further include a driver/drive train 1008 operably coupled between the motor 1004 and the cutting edge 48, and thereby the sled 41, wherein the motor 1004 is configured to controllably displace, e.g., advance, move or push, either rotationally or linearly, a position of a proximal end of the drive train 1008, to which the motor 1004 may be mechanically/electro-mechanically coupled, a controllable distance to thereby displace the cutting edge 48 and thereby, directly or indirectly, the sled 41, so as to substantially simultaneously transect the tissue grasped by the end effector 12 and deploy the staples 47 therein along, and on either side of, the transection. In certain instances, a surgical instrument 10 may include dedicated motor drivers and/or motors for firing, closure, and/or articulation.

Figure 11:
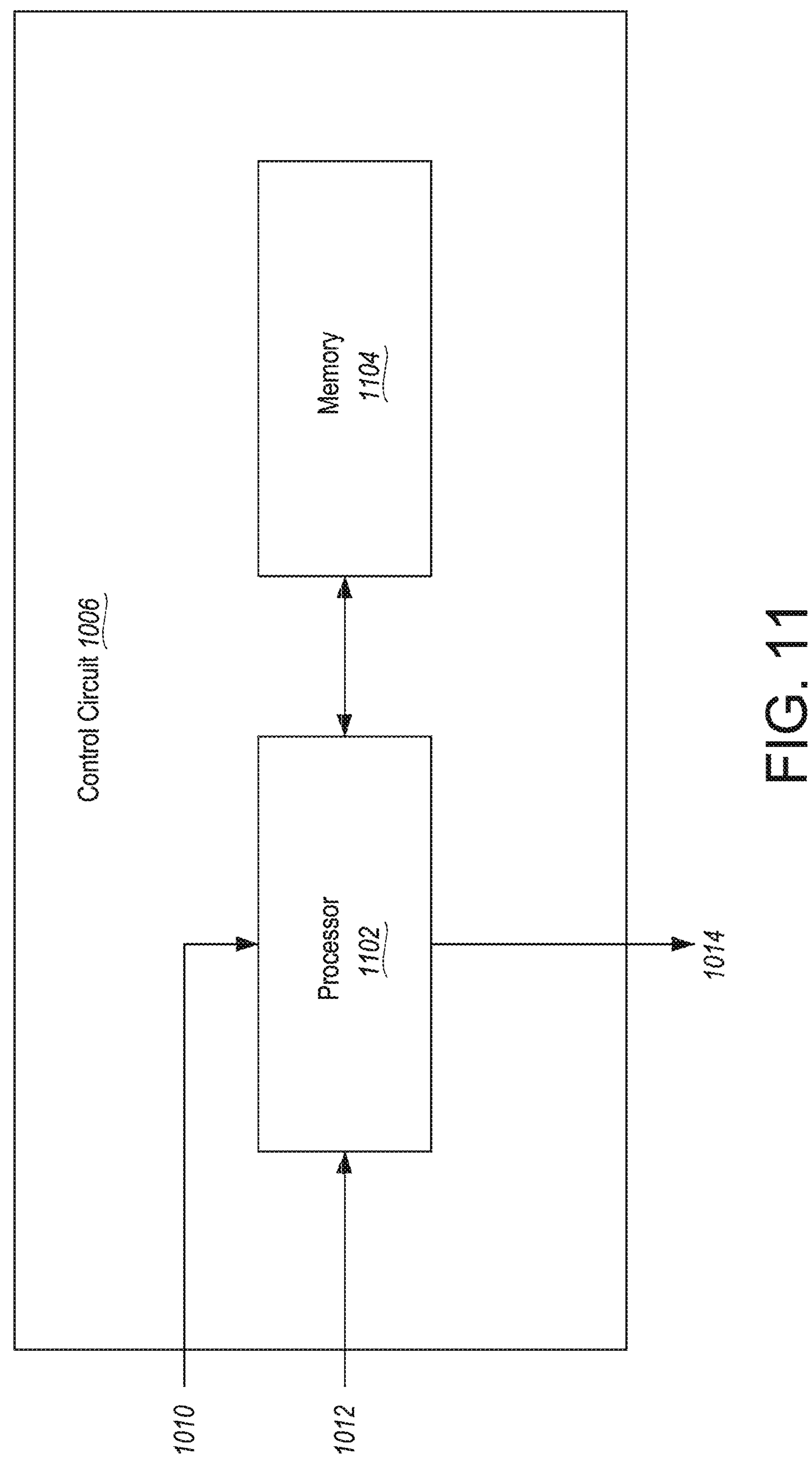
FIG. 11 shows a more detailed block diagram of the control circuit of FIG. 10 according to some embodiments.

The instrument 10 and/or a robot may further include a control circuit 1006 coupled with the motor 1004 and which is shown in more detail in FIG. 11.

In the illustrated example, the control circuit 1006 is a microcontroller and comprises one or more processors 1102 (e.g., microprocessor, microcontroller) coupled to at least one memory circuit 1104. The memory circuit 1104 stores machine-executable instructions that, when executed by the processor 1102, cause the processor 1102 to implement various processes or algorithms described herein. The processor 1102 may be any one of a number of single-core or multicore processors known in the art. The memory circuit 1104 may comprise volatile and non-volatile storage media. The processor 1102 may include an instruction processing unit and an arithmetic unit. The instruction processing unit may be configured to receive instructions from the memory circuit 1104 of this disclosure. The control circuit 1006 may comprise analog or digital circuits such as, for example, programmable logic devices (PLD), field programmable gate arrays (FPGA), discrete logic, or other hardware circuits, software, and/or firmware, or other machine executable instructions to perform the functions explained in the present description. The processor 1102 may operate according to a duty cycle which may be based on a clock rate of the processor, the duty cycle defining a frequency with which the processor may sample data or otherwise perform and/or repeat computations, e.g., with updated data.

Further to the above, the control circuit 1006 is in signal communication 1014 with the motor 1004, e.g., with a motor driver (not shown), a feedback system (not shown), a power source (not shown) (e.g. a battery, a super capacitor, or any other suitable energy source), and sensors (not shown) which, as described, sense the force/torque applied by the motor 1004 to the drive train 1008 and the current position thereof, or otherwise, an amount by which the drive train 1008 has been displaced during operation of the motor 1004.

In certain instances, the control circuit 1006 may control the motor 1004 by generating a motor set point signal 1014. The motor set point signal may be provided to the motor driver which comprises one or more circuits configured to provide a motor drive signal to the motor 1004 to drive the motor 1004 as described herein. In some examples, the motor 1004 may be a brushed DC electric motor. For example, the velocity of the motor 1004 may be proportional to the motor drive signal. In some examples, the motor 1004 may be a brushless DC electric motor and the motor drive signal may comprise a PWM signal provided to one or more stator windings of the motor 1004. Also, in some examples, the motor driver may be omitted, and the control circuit 1006 may generate the motor drive signal directly.

As described, the motor 1004 may be caused to operate so as to advance/displace the drive train 1008 at a certain rate/velocity with a certain force/torque. However, as cutting edge 48 encounters resistance, or otherwise due to friction or compliance as described herein, the operation of the motor 1004 may be impeded resulting in the torque/force applied by the motor 1004 varying as the motor attempts to maintain the directed velocity.

Accordingly, the control circuit 1006 controls a rate at which the motor 1004 is attempting to displace the proximal end of the drive train 1008 and, during displacement of the proximal end of the drive train 1008, monitors, or otherwise senses, detects or determines, such as via torque/force 1010 and drive train position 1012 sensors: the position, or amount of displacement, of the proximal end of the drive train 1008; and a force, either linear or rotational (torque) inputted to the proximal end of the drive train 1008 by the motor 1004. The current torque/force being applied by the motor 1004 may be provided by the motor 1004 encoder, motor driver or other senor coupled with the motor 1004 or the output, e.g., drive shaft/rotor, thereof. The current position, or amount of displacement, of the proximal end of the drive train 1008 may be determined via mechanical, electro-mechanical, optical and/or magnetic sensor which detect movement or a current position of the proximal end of the drive train 1008. For example, the proximal end of the drive train 1008 may feature mechanical, optical and/or magnetic indices applied to or integrated therewith which are detectable, such as by a mechanical switch, optical detector or hall effect sensor, to translate movement of the proximal end of the drive train 1008 into a signal, e.g., a digital signal from which a position or amount of movement/displacement thereof may be derived.

As described elsewhere herein, at least during displacement of the proximal end of the drive train 1008, one or more of a distance displaced by the cutting edge 48 or a force applied by the cutting edge 48 to the grasped tissue, varies, e.g., may be less than, as compared with a distance displaced by the proximal end of the drive train 1008 or a force applied thereto by the motor 1004. This variance may depend on one or more properties of the grasped tissue and/or a degree of compliance of the drive train 1008. It will be appreciated that where the force on the cutting edge 48 is absorbed by the compliance of the drive train, such as due to thick or resistant tissue, that excess force may be stored via the compliance and released when the force on the cutting edge 48 abates, e.g., as the cutting edge 48 moves into thinner or less resistant tissue, resulting in an increase the force applied by the cutting edge 48 as compared with the force applied by the motor 1004.

Figure 12:
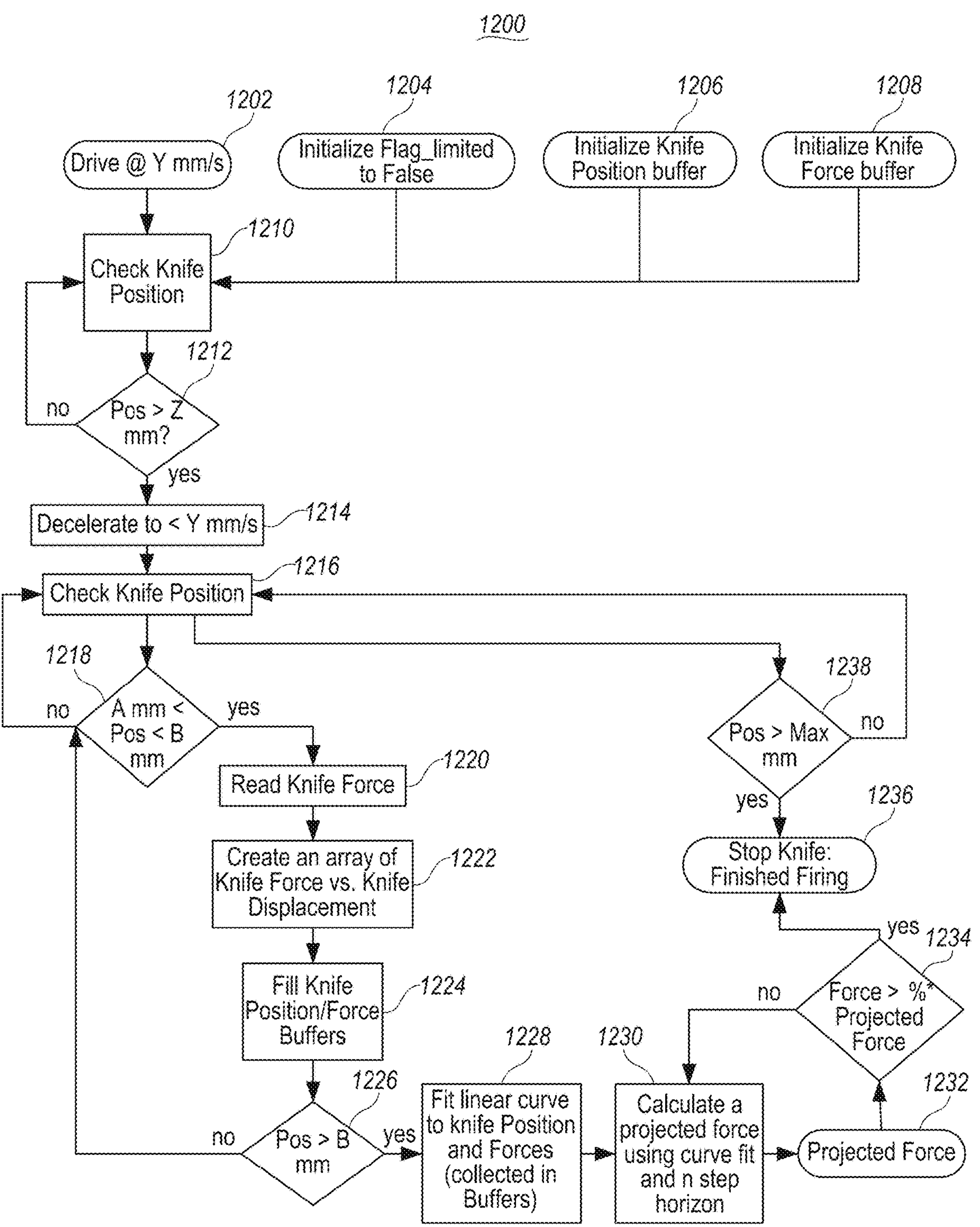
FIG. 12 shows a flow chart depicting operation of the control circuit of FIGS. 10 and 11 according to some embodiments.
Figure 13:
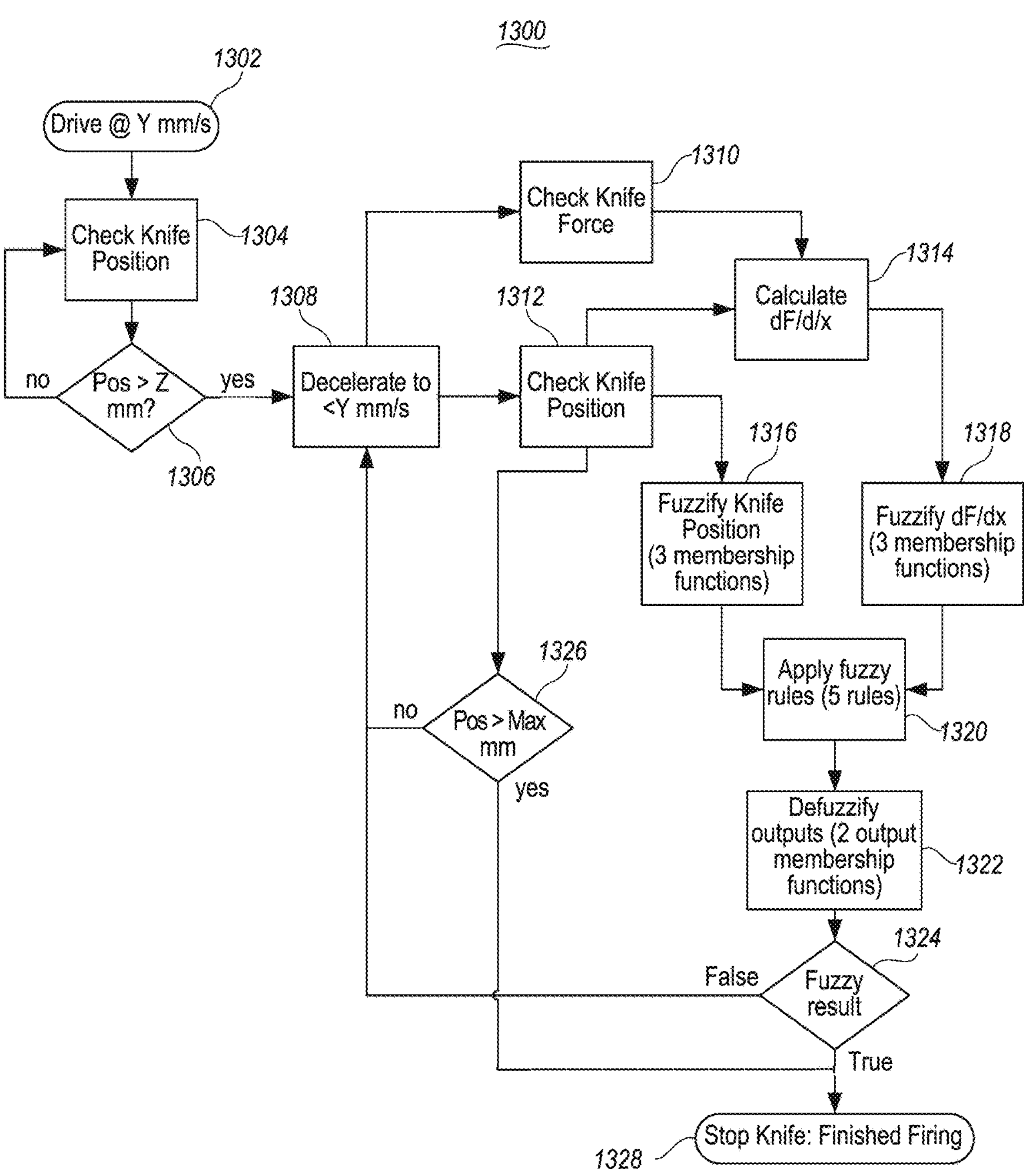
FIG. 13 shows a flow chart depicting an alternative operation of the control circuit of FIGS. 10 and 11 according to some embodiments.

As shown in FIGS. 12, 13 and 18, the control circuit 1006, during displacement of the proximal end of the drive train 1008, causes the motor 1004 to: displace the proximal end of the drive train 1008 a third distance 1804, e.g., 70-74 mm, the third distance less than the first distance, i.e., less than the maximum cutline length, with a force inputted to the proximal end of the drive train 1008 which varies so as to substantially maintain a first rate, e.g., Y mm/second, at which the motor 1004 is attempting to displace the proximal end of the drive train 1008 (Blocks 1202-1212, 1302-1306). The third distance and/or first rate may be tunable and varied so as not to impede the surgical procedure for which the instrument 10 is being used, while allowing for sufficient remaining distance/time for the remainder of the disclosed algorithm to compute a suitable projected force as will be described.

Subsequent to displacing the third distance, the control circuit 1006, during displacement of the proximal end of the drive train 1008, causes the motor 1004 to: continue to displace the proximal end of the drive train 1008 a fourth distance 1808, e.g., 2-4 mm (72-78 mm of displacement), with a force inputted to the proximal end of the drive train 1008 which varies so as to substantially maintain a second rate, e.g., <Y mm/second at which the motor 1004 is attempting to displace the proximal end of the drive train 1008, the second rate being a decelerated rate less than the first rate, such as 5-15% of the initial drive rate, during which the control circuit 1006 computes, based on the monitored force, a projected force which will be required to be inputted to the proximal end of the drive train 1008 so as to substantially maintain the second rate at which the motor 1004 is attempting to displace the proximal end of the drive train 1008 over a subsequent further distance, e.g., the next 1-4 mm (Blocks 1214-1238, 1308-1328). The computation of the projected force may be repeatedly performed, as will be described, wherein the frequency of the repetition may depend on the duty cycle of the processor 1102. It will be appreciated that the control circuit 1006 may allow, e.g., over a 1-4 mm distance from 70-74 mm, for a tunable margin of displacement 1806 over which the rate of the motor 1004 is allowed to slow down/decelerate from the first rate to the second decelerated rate before beginning the process of computing the projected force so as to allow for the displacement rate to reach a steady state, e.g., such that the dropping torque values due to the deceleration are excluded from the subsequent computation. The fourth distance and/or second rate may be tunable so as not to impede the surgical procedure for which the instrument 10 is being used, while allowing for sufficient remaining distance/time for the remainder of the disclosed algorithm to compute a suitable projected force as will be described. The subsequent distance, or number of increments thereof, for which the needed force is predicted may be implementation dependent and depend upon the amount of time needed to determine that the motor 1004 should be stopped and the amount of time it takes to actually stop the motor 1004 and the advancement of the cutting edge 48.

The control circuit 1006, during displacement of the proximal end of the drive train 1008, further causes the motor 1004 to: continue to displace 1810 the proximal end of the drive train 1008 with a force inputted to the proximal end of the drive train 1008 which varies so as to substantially maintain the second rate, e.g., <Y mm/second, at which the motor 1004 is attempting to displace the proximal end of the drive train 1008 until, e.g. over the remaining 70-77 mm of displacement, the force inputted to the proximal end of the drive train 1008 is determined to exceed a threshold, e.g., 10% to 20% over, of the computed projected force (Blocks 1230-1236, 1308-1328) 1802, upon which the control circuit 1006 stops the motor 1004. For example, if the projected force is computed to be 30 lbs and the monitored force exceeds 36 lbs, the motor 1004 is stopped. The rate applied by the motor 1004 may be the same or different from that applied computation of the projected force. Further, depending upon the implementation, different thresholds may be applied so as to determine when to stop the motor. The threshold may be calibrated so as to distinguish the force sensed based on merely encountering thicker/more resistant tissue as compared to the force sensed via the cutting edge 48, or portion thereof, impacting a physical impediment at the currently applied rate of displacement, such as the physical impediment described below, or the sled 41, or intermediate driving component therebetween, which itself was stopped due to impact with the end of the cartridge 37 or other impediment. In one embodiment, the computation of projected force continues throughout until motor 1004 is stopped.

In one embodiment, the control circuit 1006 stops the displacement, e.g., by stopping or decoupling the motor 1004, when the proximal end of the drive train 1008 has been displaced a maximum distance, e.g., >max mm (Blocks 1238, 1326). This may be implemented as a safety mechanism and absolute stopping point and may be defined based on the types of staple cartridges 37 which may be used with the instrument 10 and their physical dimensions, i.e., maximum allowable sled 41 travel distance.

Once the motor 1004 has been stopped, the control circuit 1006 may activate an indicator or otherwise generate a signal indicative of the end of cutline having been reached. The cutting edge 48 may then be retracted automatically or manually for removal and, if desired, a subsequent firing of the instrument 10.

Once the motor 1004 has been stopped, the control circuit 1006 may automatically direct the motor 1004 to reverse and retract the proximal end of the drive train 1008 and, thereby, retract the cutting edge 48 such that, for example, the jaws 16, 18 of the end effector 12 may be opened or otherwise so that the end effector 12 may be removed from the body, e.g., so that the spent staple cartridge 37 may be removed and a new staple cartridge 37 may be inserted.

The computation of the projected force and determination of when to stop the motor 1004 may be implemented in different ways. For example, as shown in FIG. 12, the computation of the projected force may include: creation of an array of then current values of the monitored force and the corresponding position, which as shown in FIG. 18 may be depicted as a graph of force vs displacement distance, as the proximal end of the drive train 1008 is displaced over the fourth distance (Blocks 1220-1222); storage of the array in a memory buffer 1104 (Block 1224); fit of a linear or best-fit curve to the stored array of monitored force and corresponding position values (Block 1228); and wherein the projected force is computed based on a projection of the fit linear/curve over one or more subsequent increments of displacement of the drive train 1008, enabling the control circuit 1006 to take preemptive action as the maximum cutline length is approached and/or achieved (Block 1230). The number of values stored in the array may depend on the displacement distance over which the values are computed, the sampling frequency or duty cycle, e.g., 2 Khz, of the processor 1102, the capacity of the memory 1104 and/or, the desired accuracy of the projected force values, which may be implementation dependent. It will be appreciated that other fitting functions may be used to determine the force trend, such as a quadratic fitting function.

In an alternative embodiment, as shown in FIG. 13, the computation of the projected force comprises: as the proximal end of the drive train 1008 is displaced over the fourth distance (Block 1308), determine the then current values of the monitored force and corresponding position (Blocks 1310, 1312), compute a change in the monitored force over distance displaced (Block 1314) and apply fuzzy logic to the current position and the change in the monitored force over distance displaced, wherein when the fuzzy logic returns a true value, the force inputted to the proximal end of the drive train 1008 is determined to exceed a threshold, e.g., 10%-20%, of the computed projected force (Blocks 1316-1324).

Fuzzification takes a crisp (single value) input and turns it into a fuzzy set (a set of values corresponding to the degree of membership for each of a set of one or more membership functions). Membership functions are functions that describe the extent that the input belongs to the fuzzy set. The maximum output of each fuzzy membership function is one, meaning the input fully part of that membership function. Fuzzy membership functions often overlap each other, and when they do, the values of each function (corresponding to an input) should sum to one and represent the degree to which the input is a part of each function wherein zero means that the input is not part of the function, one means that it is fully part of the function and any value therebetween is indicative of the degree to which the input is partially part of the function.

Membership functions may be represented as overlapping graphs with the range of possible input values forming the x axis, e.g., 1 to 100, and the degree of membership of each input value to each function depicted along the y axis, e.g., 0 to 1, where for any given input value, the degree of membership, which is implementation dependent, in the defined membership functions must add up to one. For example a membership function may be defined to cover a lower limit, e.g., input values 1-49, and another member ship function may be defined to cover an upper limit, e.g., input values 50-100, wherein the degree of membership in the lower limit function varies between 0 and 1 over the range of values 1-40, and the degree of membership in the upper limit function varies between 0 and 1 over the range of values 50-100, etc. A third middle limit membership function may further defined to cover or otherwise overlap the middle range of input values, e.g., input values 25-75, where the degree of membership in the middle limit function varies between 0 and 1 over the range of values 25-75. In this example, these three membership functions must be defined such that, for each input value, the sum of the degrees of membership in these three functions add up to one.

For example, for an input value of 35, the degree to which this input value is part of the lower limit function may be 0.25, the degree to which this input value may be part of the middle limit function may be 0.75 and the degree to which this input value may be part of the upper limit function may be 0.00, summing to a total of 1.

In the disclosed embodiments, each input to the control circuit 1006, i.e., the current displacement (position or x) of the proximal end of the drive train 1008 and the change in current force (F) being inputted to the proximal end of the drive train 1008 to maintain the current rate at which the motor 1004 is attempting to displace the displace the proximal end of the drive train 1008 as a function of change in displacement (dF/dx), may have its own set of membership functions.

The fuzzy logic rule base describes how to combine the fuzzy sets to generate an output fuzzy set. As an example, assume there are two inputs to the system and each input has three fuzzy membership functions as described above. In this example, a rule base is created that describes an output for the different combinations of the two fuzzy sets. Fuzzy logic has three operators that are used to combine the fuzzy sets: and, or, and not:

X and Y→x*y

X or Y→x+y−x*y not X→1−x

Several rules can be created using these operators. In an example implementation of the disclosed embodiments, five rules are created to combine the two fuzzy sets, the current displacement (x) of the proximal end of the drive train 1008 and the change in current force (F) being inputted to the proximal end of the drive train 1008 to maintain the current rate at which the motor 1004 is attempting to displace the displace the proximal end of the drive train 1008 as a function of change in displacement (dF/dx):

If x is far (lower limit) or df/dx is negative (lower limit), then continue.

If x is close (upper limit) and df/dx is below the threshold (middle limit), then continue.

If x is average (middle limit) and df/dx is below the threshold (middle limit), then continue.

If x is average (middle limit) and df/dx is above the threshold (upper limit), then stop.

If x is close (upper limit) and df/dx is above the threshold (upper limit), then stop.

Each fuzzy logic rule will generate an output and each of the outputs from the fuzzy logic rules are then combined using the or logic. This current rule base creates another fuzzy set with two membership functions: continue and stop. This fuzzy set is then defuzzified (transformed into precise values) to generate a single value that determines whether to continue to displace the proximal end of the drive train 1008 or to stop the motor 1004, initiate retraction, etc. In one implementation, defuzzification is performed using the following equations below, but it will be appreciated that other methods of defuzzification may be used are implementation dependent:

Result=stop>500*continue

Where 500 is a tunable parameter.

For example, using the following fuzzy sets:

input_1 (x) {0.0, 0.33, 0.67}, input_2 (df/dx) {0.0, 0.75, 0.25}

Rule outputs: {continue, stop}

1: 0.0+0.0−0.0*0.0→0.0 (continue)

2: 0.67*0.75→0.5025 (continue)

3: 0.33*0.75→0.2475 (continue)

4: 0.33*0.25→0.0825 (stop)

5: 0.67*0.25→0.1675 (stop)

Combining the rules, i.e., combine the two groups of rules into two outputs, continue and stop:

Rules: 1 & 2 & 3:

$$\text{Continue} = 0.0 + 0.5025 + 0.2475 - 0.5025 * 0.2475 - 0.0 * 0.5025 + 0.2475 - 0.5025 * 0.2475) -> 0.6256$$

Rules: 4 & 5:

Stop=0.0825+0.1675−0.0825*0.1675→0.1118

Combine the rules into a result using the equation above:

$$\text{Result} = 0.11185 > 500 * 0.6256 -> \text{False}$$

In this example, result ended as False which means to continue to displace the proximal end of the drive train 1008.

In one embodiment, a physical impediment may be provided which prevents the cutting edge 48, alone or in concert with the sled 41 and/or intermediate driving component, from moving further than the impediment, i.e., beyond the maximum cutline length. In one implementation, this physical impediment may be comprised by the distal end of the cartridge 37 itself which impedes the movement of the sled 41 and, thereby, further movement of the cutting edge 48, directly or indirectly via impeded movement of the intermediate driving component when present. The impact of the sled 41 with the end of the cartridge 37, and the resultant abrupt cessation of advancement by the cutting edge 48, may translate back through the drive train and to the motor 1004 resulting in an increase in the force applied by the motor 1004 which exceeds the projected force and results in stopping the motor 1004 as described.

In an alternative embodiment, allowing the sled 41 to impact or otherwise come into contact with the distal end of the cartridge 37 may be determined to be impractical, unsafe or otherwise not resulting in a sufficient translation of force back to the motor 1004, as for example, the cartridge 37 may not be sufficiently designed for such an impact. Accordingly, a separate or designated physical impediment may be provided, e.g., a stop or bump. This physical impediment may be formed in, or otherwise added to, one or both of the upper and lower jaws 16, 18. In one embodiment, this physical impediment, which may be referred to as a bump, stop or a trigger, may be placed in one or both of the upper and lower jaws 16, 18 so as to interrupt or prevent travel of the cutting edge 48, or the intermediate driving component if present, such as by being placed in or across one or both of the slots 42, 45 to impede the movement of the portion of the cutting edge 48 therein. The position of the physical impediment may be implementation dependent and chosen so as to result in, for example, the movement of the cutting edge 48 being impeded at the allowed maximum cutline length.

Furthermore, the physical impediment may be configured to provide a specific response, i.e., impulse, resonant or ringing response, upon being impacted by or otherwise coming into contact with the cutting edge 48, or intermediate driving component, and dissipating the force thereof as the cutting edge 48 decelerates to a stop. This specific response, when translated back through the drive train and drive train 1008 to the motor 1004, may produce a detectable response, e.g., in the frequency, magnitude or rate of change thereof, with regards to the variation in the force applied by the motor 1004 responsive thereto. For example, the placement, shape, orientation, structure, stiffness/compliance, resiliency, composition, coating, treatment and/or material, e.g., rubber, silicone, plastic, polyester, or different (higher or lower) density metal, of the physical impediment may be tuned to provide the desired response. Alternatively, the configuration of the physical impediment may be tuned to absorb, dissipate or otherwise reduce the impact force. Further, the configuration of the physical impediment may be designed to maintain the above described properties over multiple firings of the instrument, e.g., over multiple impacts by the cutting edge 48, or intermediate driving component, in accordance with the embodiments described herein.

In one embodiment, the physical impediment is formed, or otherwise provided in, the lower jaw 16 such that is below the cartridge 37 and therefore does not come into contact with grasped tissue.

In one embodiment, the physical impediment is formed in the at least one jaw 16, 18 during manufacture after the cutting edge 48 has been assembled with the at least one jaw 16, 18, so as to ease assembly of the end effector 12.

In one embodiment, the physical impediment may comprise a tab or other movable or bendable obstruction formed in or as part of the jaw 16, 18 in an un-obstructing manner to allow for assembly of the cutting edge 48 therewith and which is subsequently moved, bent or formed into an obstructing position/orientation after the cutting edge 48 has been assembled with the end effector 12.

Figure 14:
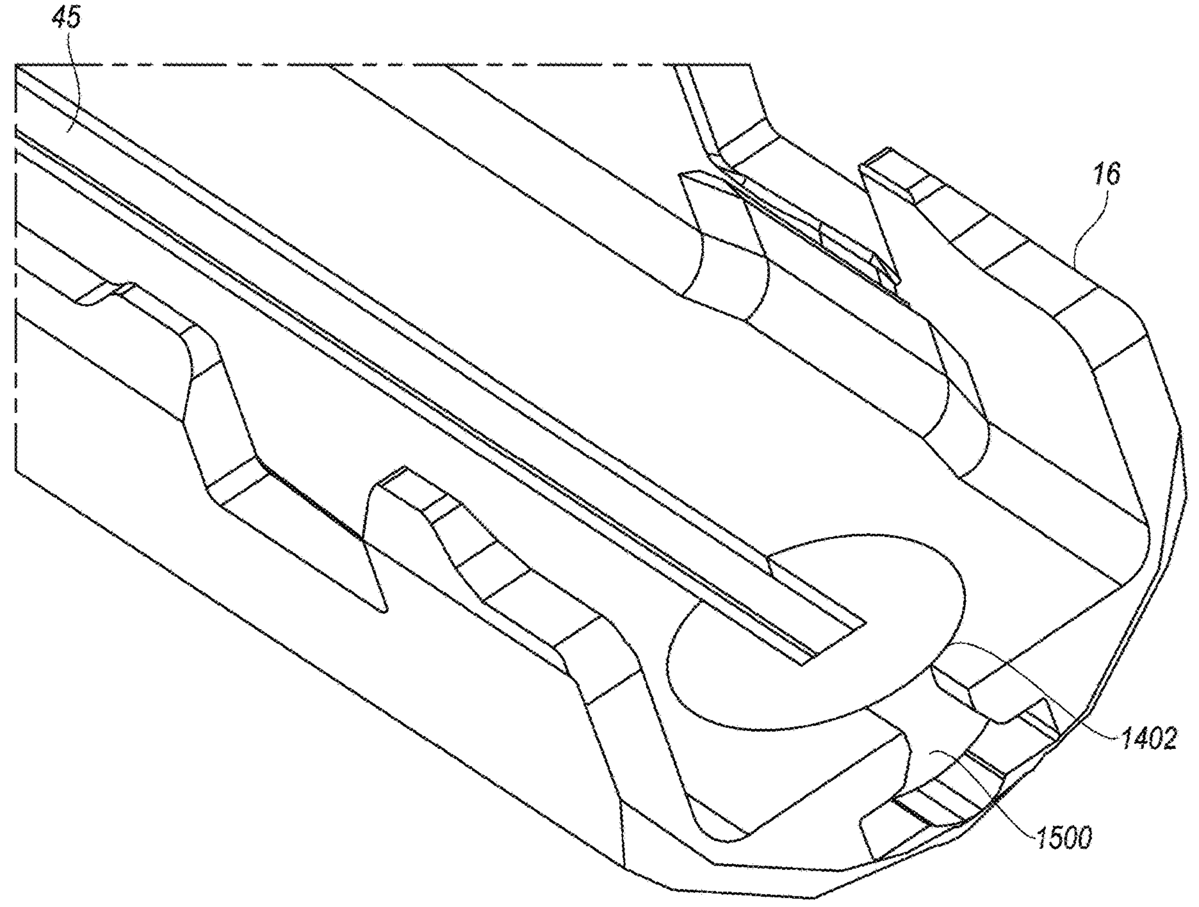
FIG. 14 depicts a perspective view of a jaw of a surgical stapling instrument including a stop inserted into a pocket therein according to some embodiments.
Figure 15:
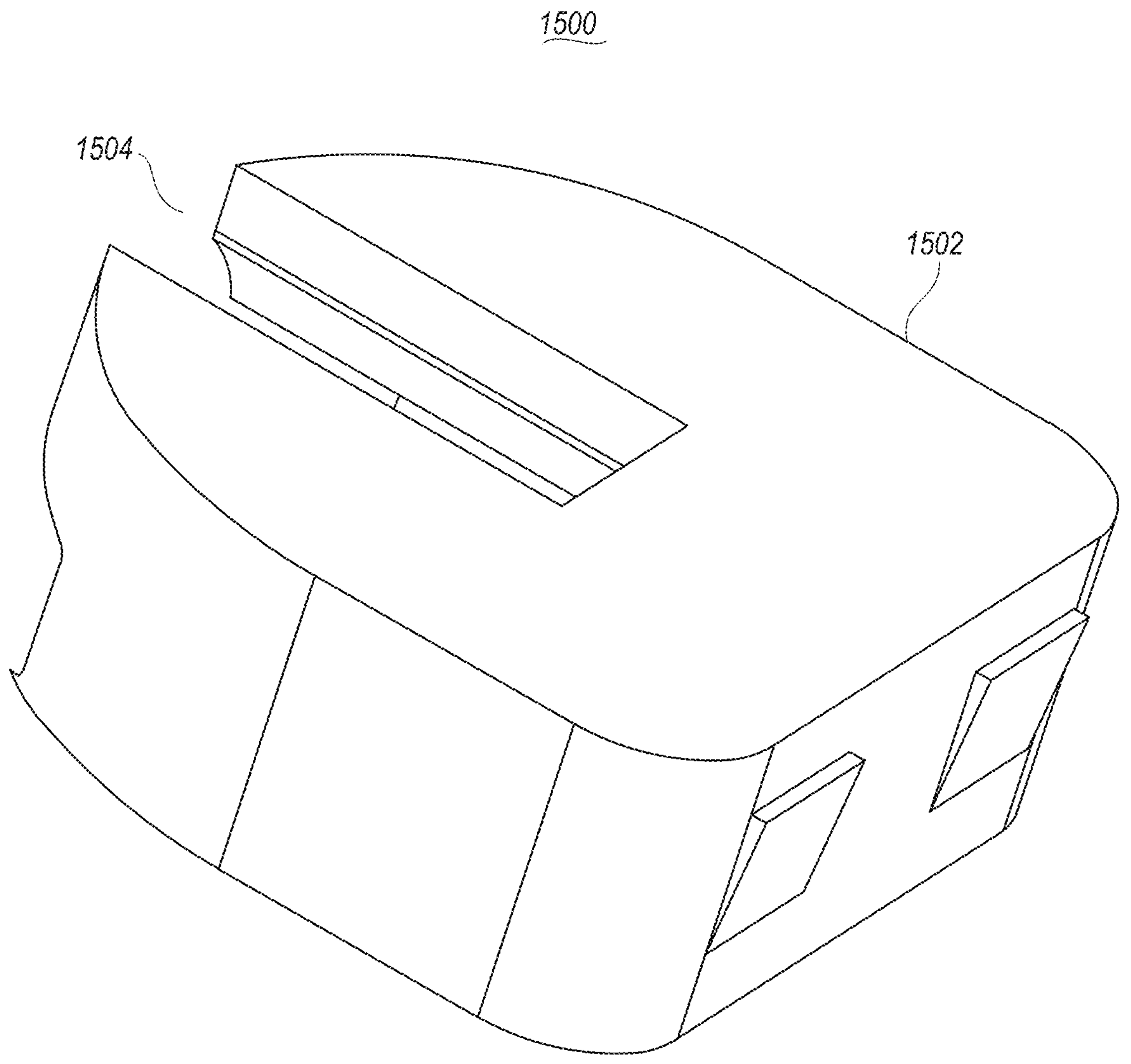
FIG. 15 depicts a perspective view of a stop for insertion into a pocket of jaw of a surgical stapling instrument according to some embodiments.

FIG. 14 depicts a perspective view of a jaw of a surgical stapling instrument including a stop inserted therein according to some embodiments. In this embodiment, a pocket 1402 is machined or otherwise formed in, for example, the lower jaw 16, into which a stop/trigger/bump is inserted at the time of manufacture, e.g., after the cutting edge 48 has been assembled therewith, such as the stop/trigger 1500 shown FIG. 15. The stop/trigger 1500 may feature a body 1502 comprised of a material, having a tuned response as described above, and having a partial slot 1504 formed therein to receive the cutting edge 48, or at least the portion thereof which travels down the slot 45. In one implementation, the slot 1504 may be fully or partially tapered, or otherwise, have a width that is less than the width of the portion of the cutting edge 45 to be received thereby, wherein as the portion of the cutting edge 45 enters the slot 1504, the cutting edge 45 contacts the inner face of the slot 1504 wherein the frictional forces act to decelerate the cutting edge 45 prior to impact/contact with the stop 1500, and/or otherwise create the desired detectable change in force.

Figure 16:
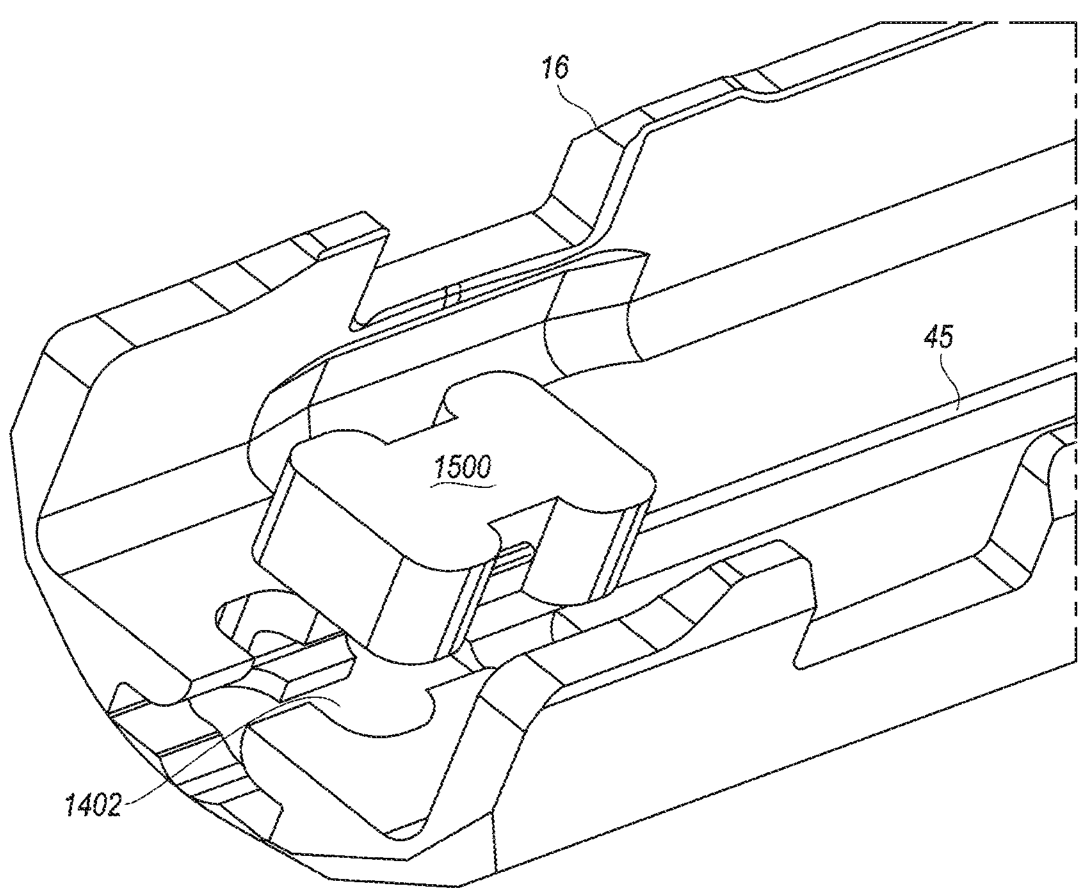
FIG. 16 depicts an exploded view of an alternative stop and lower jaw of a surgical stapling instrument according to some embodiments.
Figure 17:
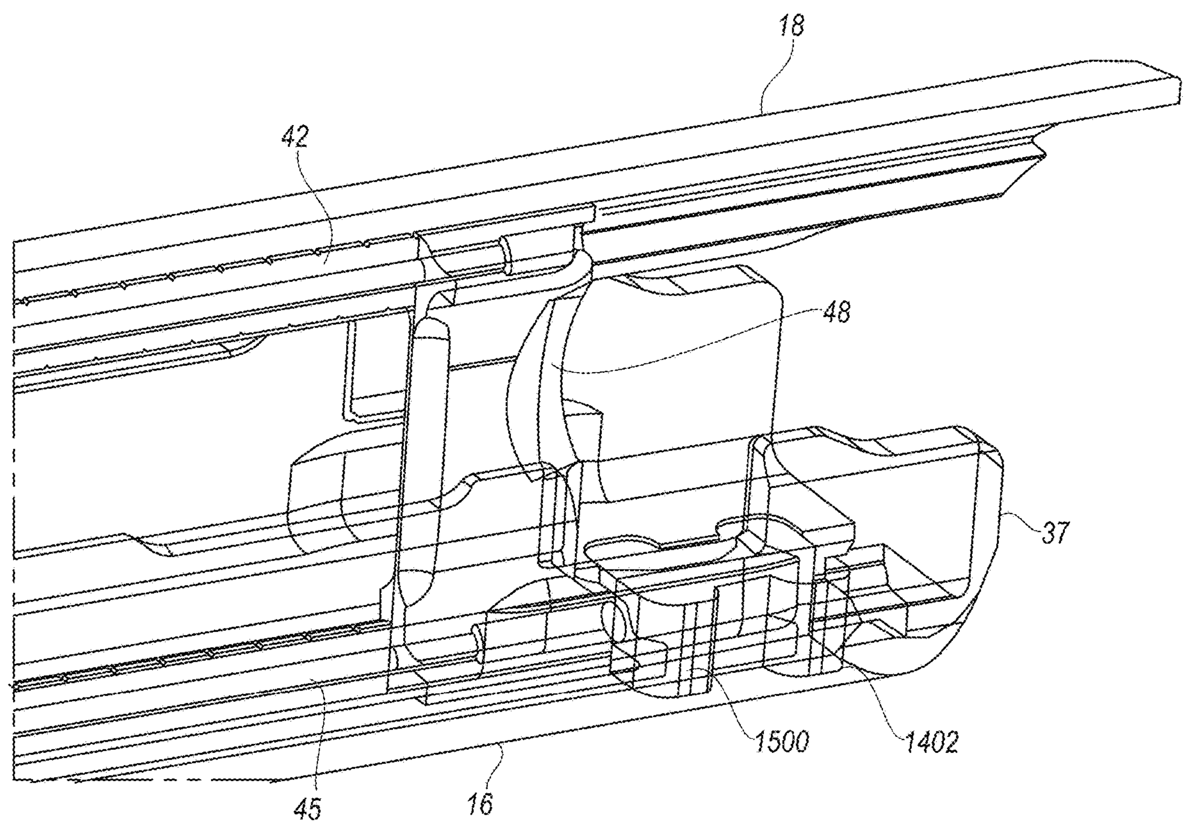
FIG. 17 depicts a perspective view of a distal end of an end effector of a surgical stapling instrument having the stop of FIG. 16 inserted in a pocket in the lower jaw thereof according to some embodiments.

FIGS. 16 and 17 depicts exploded and assembled views of an alternate stop/trigger 1500 and lower jaw 16 of a surgical stapling instrument 10 according to some embodiments. In this embodiment, the machined pocket 1402 and stop/trigger 1500 have an hour-glass shape which, upon impact/contact with the cutting edge 48, may compress in the longitudinal direction, thereby absorbing or dissipating the impact force, and/or otherwise create the desired detectable change in force.

In one embodiment, the foregoing surgical stapling instrument 10 further includes: a handle 20 comprising the motor 1004 and control circuit 1006; an articulation joint 11; a shaft 22 extending from a handle 20 to the articulation joint 11 to which the end effector 12 is coupled, wherein the shaft 22 comprises the drive train 1008; and wherein the end effector 12 comprises a firing beam 14 operably coupled with the drive train 1008 and comprising the cutting edge 48; and wherein said articulation joint 11 permits the end effector 12 to be articulated and maintained in one or more directions relative to a longitudinal axis of the shaft 22 via application of a holding force. In one embodiment, the threshold of the computed projected force is determined to be less than the holding force.

In one embodiment, the foregoing surgical stapling instrument 10 is configured to be attached and operated by a robot.

VI. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A control circuit (1006) for controlling a surgical instrument (10), the surgical instrument (10) comprising an end effector (12) configured to grasp tissue, the end effector (12) comprising jaws (16, 18) comprising a cutting edge (48) configured to be displaced a first distance from a proximal end to a distal end of the jaws (16, 18) such that at least a portion of the cutting edge (48) transects tissue grasped by the end effector, the jaws (16, 18) further configured to receive a staple cartridge (37) seatable in one of the jaws (16, 18) and including a sled (41) and staples (47), the sled (41) configured to be displaced a second distance from a proximal end to a distal end of the staple cartridge (37) to deploy the staples (47) into the tissue grasped by the end effector (12) along the transection, the surgical instrument (10) further comprising a motor (1004) located external to the end effector (12) and a drive train (1008) operably coupled between the motor (1004) and the cutting edge (48) and the sled (41), wherein the motor (1004) is configured to controllably displace a position of a proximal end of the drive train (1008) a controllable distance to displace the cutting edge (48) and the sled (41) so as to substantially simultaneously transect the tissue grasped by the end effector (12)

and deploy the staples (47) therein along, and on either side of, the transection, the control circuit (1006) comprising:

a processor and a memory coupled therewith, the memory having stored therein computer readable instructions which, when executed by the processor, cause the processor to:

control a rate at which the motor (1004) is attempting to displace the proximal end of the drive train (1008); and monitor during displacement of the proximal end of the drive train (1008):

the position of the proximal end of the drive train (1008); and a force inputted to the proximal end of the drive train (1008) by the motor (1004); and during displacement of the proximal end of the drive train (1008), cause the motor (1004) to:

displace the proximal end of the drive train (1008) a third distance, the third distance less than the first distance, with a force inputted to the proximal end of the drive train (1008) which varies so as to substantially maintain a first rate at which the motor (1004) is attempting to displace the proximal end of the drive train (1008);

subsequent to displacing the third distance, continue to displace the proximal end of the drive train (1008) a fourth distance with a force inputted to the proximal end of the drive train (1008) which varies so as to substantially maintain a second rate at which the motor (1004) is attempting to displace the proximal end of the drive train (1008), the second rate less than the first rate, during which the control circuit (1006) computes, based on the monitored force, a projected force which will be required to be inputted to the proximal end of the drive train (1008) so as to substantially maintain the second rate at which the motor (1004) is attempting to displace the proximal end of the drive train (1008) over a subsequent further distance; and continue to displace the proximal end of the drive train (1008) with a force inputted to the proximal end of the drive train (1008) which varies so as to substantially maintain the second rate at which the motor (1004) is attempting to displace the proximal end of the drive train (1008) until the force inputted to the proximal end of the drive train (1008) is determined to exceed a threshold of the computed projected force.

Example 2

The control circuit (1006) of Example 1, wherein at least during displacement of the proximal end of the drive train (1008), one or more of a distance displaced by the cutting edge (48) or a force applied by the cutting edge (48) to the grasped tissue, varies as compared with a distance displaced by the proximal end of the drive train (1008) or a force applied thereto by the motor (1004).

Example 3

The control circuit (1006) of Example 2, wherein the variance depends on one or more properties of the grasped tissue and/or a degree of compliance of the drive train (1008).

Example 4

The control circuit (1006) of any of Examples 1-3, wherein the control circuit (1006) stops the displacement when the proximal end of the drive train (1008) has been displaced a maximum distance.

Example 5

The control circuit (1006) of any of Examples 1-4, wherein the cutting edge (48) is physically impeded from exceeding the first distance.

Example 6

The control circuit (1006) of any of Examples 1-5, wherein the physical impediment (1500) is formed in the at least one jaw (16, 18) during manufacture after the cutting edge (48) has been assembled with the at least one jaw (16, 18).

Example 7

The control circuit (1006) of any of Examples 1-6, wherein the physical impediment (1500) is characterized by a property which results in a distinguishable change in the monitored force inputted to the proximal end of the drive train (1008) to maintain the second rate when at least a portion of the cutting edge (48) impacts, encounters or otherwise makes contact with the physical impediment (1500).

Example 8

The control circuit (1006) of any of Examples 1-7, wherein the computation of the projected force comprises:

creation of an array of then current values of the monitored force and the corresponding position as the proximal end of the drive train (1008) is displaced over the fourth distance;

storage of the array in a memory buffer (1104);

fit of one of a linear or best-fit curve to the stored array of monitored force and corresponding position values; and wherein the projected force is computed based on a projection of the fit linear or best-fit curve over one or more subsequent increments of displacement of the drive train (1008).

Example 9

The control circuit (1006) of any of Examples 1-7, wherein the computation of the projected force comprises:

as the proximal end of the drive train (1008) is displaced over the fourth distance, determine the then current values of the monitored force and corresponding position, compute a change in the monitored force over distance displaced and apply fuzzy logic to the current position and the change in the monitored force over distance displaced, wherein when the fuzzy logic returns a true value, the force inputted to the proximal end of the drive train (1008) is determined to exceed a threshold of the computed projected force.

Example 10

The control circuit (1006) of any of Examples 1-9, wherein the surgical instrument (10) comprises a handle (20) and a shaft (22), a proximal end of the shaft (22) being coupled with a distal end of the handle (20), the distal end of the shaft (22) being coupled with the end effector (12), wherein the motor (1004) is located in the handle (20) and the drive train (1008) is located in the shaft (22) and extends from the proximal end of the shaft (22) to the distal end of the shaft (22).

Example 11

The control circuit (1006) of any of Examples 1-10, wherein the drive train (1008) comprises multiple linked components.

Example 12

The control circuit (1006) of any of Examples 1-11, further comprising:

a handle (20) comprising the motor (1004) and control circuit (1006);

an articulation joint (11);

a shaft (22) extending from a handle (20) to the articulation joint (11) to which the end effector (12) is coupled, wherein the shaft (22) comprises the drive train (1008); and wherein the end effector (12) comprises a firing beam (14) operably coupled with the drive train (1008) and comprising the cutting edge (48); and wherein said articulation joint (11) permits the end effector (12) to be articulated and maintained in one or more directions relative to a longitudinal axis of the shaft via application of a holding force.

Example 13

The control circuit (1006) of any of Examples 1-12, wherein the threshold of the computed projected force is less than the holding force.

Example 14

The control circuit (1006) of any of Examples 1-13, wherein the surgical stapling instrument (10) is configured to be attached and operated by a robot.

Example 15

A surgical stapling instrument (10) comprising:

an end effector (12) configured to grasp tissue, the end effector (12) comprising:

jaws (16, 18) comprising a cutting edge (48) configured to be displaced a first distance from a proximal end to a distal end of the jaws (16, 18) such that at least a portion of the cutting edge (48) transects tissue grasped by the end effector, the jaws (16, 18) further configured to receive a staple cartridge (37) seatable in one of the jaws (16, 18) and including a sled (41) and staples (47), the sled (41) configured to be displaced a second distance from a proximal end to a distal end of the staple cartridge (37) to deploy the staples (47) into the tissue grasped by the end effector (12) along the transection;

a motor (1004) located external to the end effector (12); and a drive train (1008) operably coupled between the motor (1004) and the cutting edge (48) and the sled (41), wherein the motor (1004) is configured to controllably displace a position of a proximal end of the drive train (1008) a controllable distance to displace the cutting edge (48) and the sled (41) so as to substantially simultaneously transect the tissue grasped by the end effector (12) and deploy the staples (47) therein along, and on either side of, the transection; and the control circuit (1006) of any of Examples 1-14.

Example 16

A method of operating a surgical instrument (10), the surgical instrument (10) comprising an end effector (12) configured to grasp tissue, the end effector (12) comprising jaws (16, 18) comprising a cutting edge (48) configured to be displaced a first distance from a proximal end to a distal end of the jaws (16, 18) such that at least a portion of the cutting edge (48) transects tissue grasped by the end effector, the jaws (16, 18) further configured to receive a staple cartridge (37) seatable in one of the jaws (16, 18) and including a sled (41) and staples (47), the sled (41) configured to be displaced a second distance from a proximal end to a distal end of the staple cartridge (37) to deploy the staples (47) into the tissue grasped by the end effector (12) along the transection, the surgical instrument (10) further comprising a motor (1004) located external to the end effector (12) and a drive train (1008) operably coupled between the motor (1004) and the cutting edge (48) and the sled (41), wherein the motor (1004) is configured to controllably displace a position of a proximal end of the drive train (1008) a controllable distance to displace the cutting edge (48) and the sled (41) so as to substantially simultaneously transect the tissue grasped by the end effector (12) and deploy the staples (47) therein along, and on either side of, the transection, the method comprising:

controlling a rate at which the motor (1004) is attempting to displace the proximal end of the drive train (1008); and monitoring:

the position of the proximal end of the drive train (1008); and a force inputted to the proximal end of the drive train (1008) by the motor (1004); and during displacement of the proximal end of the drive train (1008), causing the motor (1004) to:

displace the proximal end of the drive train (1008) a third distance, the third distance less than the first distance, with a force inputted to the proximal end of the drive train (1008) which varies so as to substantially maintain a first rate at which the motor (1004) is attempting to displace the proximal end of the drive train (1008);

subsequent to attempting to displace the third distance, continue to displace the proximal end of the drive train (1008) a fourth distance with a force inputted to the proximal end of the drive train (1008) which varies so as to substantially maintain a second rate at which the motor (1004) is attempting to displace the proximal end of the drive train (1008), the second rate less than the first rate, during which the control circuit (1006) computes, based on the monitored force, a projected force which will be required to be inputted to the proximal end of the drive train (1008) so as to substantially maintain the second rate at which the motor (1004) is attempting to displace the proximal end of the drive train (1008) over a subsequent further distance; and continue to displace the proximal end of the drive train (1008) with a force inputted to the proximal end of the drive train (1008) which varies so as to substantially maintain the second rate at which the motor (1004) is attempting to displace the proximal end of the drive train (1008) until the force inputted to the proximal end of the drive train (1008) is determined to exceed a threshold of the computed projected force.

Example 17

The method of Example 16, wherein the computation of the projected force comprises:

creating an array of then current values of the monitored force and the corresponding position as the proximal end of the drive train (1008) is displaced over the fourth distance;

storing the array in a memory buffer (1104);

fitting of one of a linear or best-fit curve to the stored array of monitored force and corresponding position values; and wherein the projected force is computed based on a projection of the fit linear or best-fit curve over one or more subsequent increments of displacement of the drive train (1008).

Example 18

The method of Example 16, wherein the computation of the projected force comprises:

as the proximal end of the drive train (1008) is displaced over the fourth distance, determining the then current values of the monitored force and corresponding position, computing a change in the monitored force over distance displaced and apply fuzzy logic to the current position and the change in the monitored force over distance displaced, wherein when the fuzzy logic returns a true value, the force inputted to the proximal end of the drive train (1008) is determined to exceed a threshold of the computed projected force.

Example 19

The method of any of Examples 16-18, wherein the cutting edge (48) is physically impeded from exceeding the first distance.

Example 20

The method of any of Examples 16-19, further comprising forming the physical impediment (1500) in the at least one jaw (16, 18) during manufacture after the cutting edge (48) has been assembled with the at least one jaw (16, 18).

The following clauses also relate to various non-exhaustive ways in which the teachings herein may be combined or applied.

1. A surgical stapling instrument (10) comprising:

an end effector (12) configured to grasp tissue, the end effector (12) comprising:

jaws (16, 18) comprising a cutting edge (48) configured to be displaced a first distance from a proximal end to a distal end of the jaws (16, 18) such that at least a portion of the cutting edge (48) transects tissue grasped by the end effector, the jaws (16, 18) further configured to receive a staple cartridge (37) seatable in one of the jaws (16, 18) and including a sled (41) and staples (47), the sled (41) configured to be displaced a second distance from a proximal end to a distal end of the staple cartridge (37) to deploy the staples (47) into the tissue grasped by the end effector (12) along the transection;

a motor (1004) located external to the end effector (12); and a drive train (1008) operably coupled between the motor (1004) and the cutting edge (48) and the sled (41), wherein the motor (1004) is configured to controllably displace a position of a proximal end of the drive train (1008) a controllable distance to displace the cutting edge (48) and the sled (41) so as to substantially simultaneously transect the tissue grasped by the end effector (12) and deploy the staples (47) therein along, and on either side of, the transection;

a control circuit (1006) coupled with the motor (1004) and which controls a rate at which the motor (1004) is attempting to displace the proximal end of the drive train (1008) and, during displacement of the proximal end of the drive train (1008), monitors:

the position of the proximal end of the drive train (1008); and a force inputted to the proximal end of the drive train (1008) by the motor (1004); and wherein the control circuit (1006), during displacement of the proximal end of the drive train (1008), causes the motor (1004) to:

displace the proximal end of the drive train (1008) a third distance, the third distance less than the first distance, with a force inputted to the proximal end of the drive train (1008) which varies so as to substantially maintain a first rate at which the motor (1004) is attempting to displace the proximal end of the drive train (1008);

subsequent to displacing the third distance, continue to displace the proximal end of the drive train (1008) a fourth distance with a force inputted to the proximal end of the drive train (1008) which varies so as to substantially maintain a second rate at which the motor (1004) is attempting to displace the proximal end of the drive train (1008), the second rate less than the first rate, during which the control circuit (1006) computes, based on the monitored force, a projected force which will be required to be inputted to the proximal end of the drive train (1008) so as to substantially maintain the second rate at which the motor (1004) is attempting to displace the proximal end of the drive train (1008) over a subsequent further distance; and continue to displace the proximal end of the drive train (1008) with a force inputted to the proximal end of the drive train (1008) which varies so as to substantially maintain the second rate at which the motor (1004) is attempting to displace the proximal end of the drive train (1008) until the force inputted to the proximal end of the drive train (1008) is determined to exceed a threshold of the computed projected force.

2. The surgical stapling instrument (10) of claim 1, wherein at least during displacement of the proximal end of the drive train (1008), one or more of a distance displaced by the cutting edge (48) or a force applied by the cutting edge (48) to the grasped tissue, varies as compared with a distance displaced by the proximal end of the drive train (1008) or a force applied thereto by the motor (1004).

3. The surgical stapling instrument (10) of claim 2, wherein the variance depends on one or more properties of the grasped tissue and/or a degree of compliance of the drive train (1008).

4. The surgical stapling instrument (10) of claim 1, wherein the control circuit (1006) stops the displacement when the proximal end of the drive train (1008) has been displaced a maximum distance.

5. The surgical stapling instrument (10) of claim 1, wherein the cutting edge (48) is physically impeded from exceeding the first distance.

6. The surgical stapling instrument (10) of claim 5, wherein the physical impediment (1500) is formed in the at least one jaw (16, 18) during manufacture after the cutting edge (48) has been assembled with the at least one jaw (16, 18).

7. The surgical stapling instrument (10) of claim 5, wherein the physical impediment (1500) is characterized by a property which results in a distinguishable change in the monitored force inputted to the proximal end of the drive train (1008) to maintain the second rate when at least a portion of the cutting edge (48) impacts, encounters or otherwise makes contact with the physical impediment (1500).

8. The surgical stapling instrument (10) of claim 1, wherein the computation of the projected force comprises:
- creation of an array of then current values of the monitored force and the corresponding position as the proximal end of the drive train (1008) is displaced over the fourth distance;
- storage of the array in a memory buffer (1104);
- fit of one of a linear or best-fit curve to the stored array of monitored force and corresponding position values; and
- wherein the projected force is computed based on a projection of the fit linear or best-fit curve over one or more subsequent increments of displacement of the drive train (1008).

9. The surgical stapling instrument (10) of claim 1, wherein the computation of the projected force comprises:
- as the proximal end of the drive train (1008) is displaced over the fourth distance, determine the then current values of the monitored force and corresponding position, compute a change in the monitored force over distance displaced and apply fuzzy logic to the current position and the change in the monitored force over distance displaced, wherein when the fuzzy logic returns a true value, the force inputted to the proximal end of the drive train (1008) is determined to exceed a threshold of the computed projected force.

10. The surgical stapling instrument (10) of claim 1, wherein the surgical instrument (10) comprises a handle (20) and a shaft (22), a proximal end of the shaft (22) being coupled with a distal end of the handle (20), the distal end of the shaft (22) being coupled with the end effector (12), wherein the motor (1004) is located in the handle (20) and the drive train (1008) is located in the shaft (22) and extends from the proximal end of the shaft (22) to the distal end of the shaft (22).

11. The surgical stapling instrument (10) of claim 1, wherein the drive train (1008) comprises multiple linked components.

12. The surgical stapling instrument (10) of claim 1, further comprising:
- a handle (20) comprising the motor (1004) and control circuit (1006);
- an articulation joint (11);
- a shaft (22) extending from a handle (20) to the articulation joint (11) to which the end effector (12) is coupled, wherein the shaft (22) comprises the drive train (1008); and
- wherein the end effector (12) comprises a firing beam (14) operably coupled with the drive train (1008) and comprising the cutting edge (48); and
- wherein said articulation joint (11) permits the end effector (12) to be articulated and maintained in one or more directions relative to a longitudinal axis of the shaft via application of a holding force.

13. The surgical stapling instrument (10) of claim 12, wherein the threshold of the computed projected force is less than the holding force.

14. The surgical stapling instrument (10) of claim 1, wherein the surgical stapling instrument (10) is configured to be attached and operated by a robot.

15. A control circuit (1006) for controlling a surgical instrument (10), the surgical instrument (10) comprising an end effector (12) configured to grasp tissue, the end effector (12) comprising jaws (16, 18) comprising a cutting edge (48) configured to be displaced a first distance from a proximal end to a distal end of the jaws (16, 18) such that at least a portion of the cutting edge (48) transects tissue grasped by the end effector, the jaws (16, 18) further configured to receive a staple cartridge (37) seatable in one of the jaws (16, 18) and including a sled (41) and staples (47), the sled (41) configured to be displaced a second distance from a proximal end to a distal end of the staple cartridge (37) to deploy the staples (47) into the tissue grasped by the end effector (12) along the transection, the surgical instrument (10) further comprising a motor (1004) located external to the end effector (12) and a drive train (1008) operably coupled between the motor (1004) and the cutting edge (48) and the sled (41), wherein the motor (1004) is configured to controllably displace a position of a proximal end of the drive train (1008) a controllable distance to displace the cutting edge (48) and the sled (41) so as to substantially simultaneously transect the tissue grasped by the end effector (12) and deploy the staples (47) therein along, and on either side of, the transection, the control circuit (1006) comprising:
- a processor and a memory coupled therewith, the memory having stored therein computer readable instructions which, when executed by the processor, cause the processor to:
  - control a rate at which the motor (1004) is attempting to displace the proximal end of the drive train (1008); and
  - monitor during displacement of the proximal end of the drive train (1008):
    - the position of the proximal end of the drive train (1008); and
    - a force inputted to the proximal end of the drive train (1008) by the motor (1004); and
- during displacement of the proximal end of the drive train (1008), cause the motor (1004) to:
  - displace the proximal end of the drive train (1008) a third distance, the third distance less than the first distance, with a force inputted to the proximal end of the drive train (1008) which varies so as to substantially maintain a first rate at which the motor (1004) is attempting to displace the proximal end of the drive train (1008);
  - subsequent to displacing the third distance, continue to displace the proximal end of the drive train (1008) a fourth distance with a force inputted to the proximal end of the drive train (1008) which varies so as to substantially maintain a second rate at which the motor (1004) is attempting to displace the proximal end of the drive train (1008), the second rate less than the first rate, during which the control circuit (1006) computes, based on the monitored force, a projected force which will be required to be inputted to the proximal end of the drive train (1008) so as to substantially maintain the second rate at which the motor (1004) is attempting to displace the proximal end of the drive train (1008) over a subsequent further distance; and continue to displace the proximal end of the drive train (1008) with a force inputted to the proximal end of the drive train (1008) which varies so as to substantially maintain the second rate at which the motor (1004) is attempting to displace the proximal end of the drive train (1008) until the force inputted to the proximal end of the drive train (1008) is determined to exceed a threshold of the computed projected force.

16. The control circuit (1006) of claim 15, wherein the computation of the projected force comprises:

creation of an array of then current values of the monitored force and the corresponding position as the proximal end of the drive train (1008) is displaced over the fourth distance;

storage of the array in a memory buffer (1104);

fit of one of a linear or best-fit curve to the stored array of monitored force and corresponding position values; and wherein the projected force is computed based on a projection of the fit linear or best-fit curve over one or more subsequent increments of displacement of the drive train (1008).

17. The control circuit (1006) of claim 15, wherein the computation of the projected force comprises:

as the proximal end of the drive train (1008) is displaced over the fourth distance, determine the then current values of the monitored force and corresponding position, compute a change in the monitored force over distance displaced and apply fuzzy logic to the current position and the change in the monitored force over distance displaced, wherein when the fuzzy logic returns a true value, the force inputted to the proximal end of the drive train (1008) is determined to exceed a threshold of the computed projected force.

18. The control circuit (1006) of claim 15, wherein the cutting edge (48) is physically impeded from exceeding the first distance.

19. The control circuit (1006) of claim 18, wherein the physical impediment (1500) is formed in the at least one jaw (16, 18) during manufacture after the cutting edge (48) has been assembled with the at least one jaw (16, 18).

20. The control circuit (1006) of claim 18, wherein the physical impediment (1500) is characterized by a property which results in a distinguishable change in the monitored force inputted to the proximal end of the drive train (1008) to maintain the second rate when at least a portion of the cutting edge (48) impacts, encounters or otherwise makes contact with the physical impediment (1500).

21. A method of operating a surgical instrument (10), the surgical instrument (10) comprising an end effector (12) configured to grasp tissue, the end effector (12) comprising jaws (16, 18) comprising a cutting edge (48) configured to be displaced a first distance from a proximal end to a distal end of the jaws (16, 18) such that at least a portion of the cutting edge (48) transects tissue grasped by the end effector, the jaws (16, 18) further configured to receive a staple cartridge (37) seatable in one of the jaws (16, 18) and including a sled (41) and staples (47), the sled (41) configured to be displaced a second distance from a proximal end to a distal end of the staple cartridge (37) to deploy the staples (47) into the tissue grasped by the end effector (12) along the transection, the surgical instrument (10) further comprising a motor (1004) located external to the end effector (12) and a drive train (1008) operably coupled between the motor (1004) and the cutting edge (48) and the sled (41), wherein the motor (1004) is configured to controllably displace a position of a proximal end of the drive train (1008) a controllable distance to displace the cutting edge (48) and the sled (41) so as to substantially simultaneously transect the tissue grasped by the end effector (12) and deploy the staples (47) therein along, and on either side of, the transection, the method comprising:

controlling a rate at which the motor (1004) is attempting to displace the proximal end of the drive train (1008); and monitoring:

the position of the proximal end of the drive train (1008); and a force inputted to the proximal end of the drive train (1008) by the motor (1004); and during displacement of the proximal end of the drive train (1008), causing the motor (1004) to:

displace the proximal end of the drive train (1008) a third distance, the third distance less than the first distance, with a force inputted to the proximal end of the drive train (1008) which varies so as to substantially maintain a first rate at which the motor (1004) is attempting to displace the proximal end of the drive train (1008);

subsequent to attempting to displace the third distance, continue to displace the proximal end of the drive train (1008) a fourth distance with a force inputted to the proximal end of the drive train (1008) which varies so as to substantially maintain a second rate at which the motor (1004) is attempting to displace the proximal end of the drive train (1008), the second rate less than the first rate, during which the control circuit (1006) computes, based on the monitored force, a projected force which will be required to be inputted to the proximal end of the drive train (1008) so as to substantially maintain the second rate at which the motor (1004) is attempting to displace the proximal end of the drive train (1008) over a subsequent further distance; and continue to displace the proximal end of the drive train (1008) with a force inputted to the proximal end of the drive train (1008) which varies so as to substantially maintain the second rate at which the motor (1004) is attempting to displace the proximal end of the drive train (1008) until the force inputted to the proximal end of the drive train (1008) is determined to exceed a threshold of the computed projected force.

22. The method of claim 21, wherein the computation of the projected force comprises:

creating an array of then current values of the monitored force and the corresponding position as the proximal end of the drive train (1008) is displaced over the fourth distance;

storing the array in a memory buffer (1104);

fitting of one of a linear or best fit curve to the stored array of monitored force and corresponding position values; and wherein the projected force is computed based on a projection of the fit linear or best-fit curve over one or more subsequent increments of displacement of the drive train (1008).

23. The method of claim 21, wherein the computation of the projected force comprises:

as the proximal end of the drive train (1008) is displaced over the fourth distance, determining the then current values of the monitored force and corresponding position, computing a change in the monitored force over distance displaced and apply fuzzy logic to the current position and the change in the monitored force over distance displaced, wherein when the fuzzy logic returns a true value, the force inputted to the proximal end of the drive train (1008) is determined to exceed a threshold of the computed projected force.

24. The method of claim 21, wherein the cutting edge (48) is physically impeded from exceeding the first distance.

25. The method of claim 23, further comprising forming the physical impediment (1500) in the at least one jaw (16, 18) during manufacture after the cutting edge (48) has been assembled with the at least one jaw (16, 18).

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467,648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical stapling instrument comprising:

an end effector configured to grasp tissue, the end effector comprising:

jaws comprising a cutting edge configured to be displaced a first distance from a proximal end to a distal end of the jaws such that at least a portion of the cutting edge transects tissue grasped by the end effector, the jaws further configured to receive a staple cartridge seatable in one of the jaws and including a sled and staples, the sled configured to be displaced a second distance from a proximal end to a distal end of the staple cartridge to deploy the staples into the tissue grasped by the end effector along the transection;

a motor located external to the end effector; and a drive train operably coupled between the motor and the cutting edge and the sled, wherein the motor is configured to controllably displace a position of a proximal end of the drive train a controllable distance to displace the cutting edge and the sled so as to substantially simultaneously transect the tissue grasped by the end effector and deploy the staples therein along, and on either side of, the transection;

a control circuit coupled with the motor and which controls a rate at which the motor is attempting to displace the proximal end of the drive train and, during displacement of the proximal end of the drive train, monitors:

the position of the proximal end of the drive train; and a force inputted to the proximal end of the drive train by the motor; and wherein the control circuit, during displacement of the proximal end of the drive train, causes the motor to:

displace the proximal end of the drive train a third distance, the third distance less than the first distance, with a force inputted to the proximal end of the drive train which varies so as to substantially maintain a first rate at which the motor is attempting to displace the proximal end of the drive train;

subsequent to displacing the third distance, continue to displace the proximal end of the drive train a fourth distance with a force inputted to the proximal end of the drive train which varies so as to substantially maintain a second rate at which the motor is attempting to displace the proximal end of the drive train, the second rate less than the first rate, during which the control circuit computes, based on the monitored force, a projected force which will be required to be inputted to the proximal end of the drive train so as to substantially maintain the second rate at which the motor is attempting to displace the proximal end of the drive train over a subsequent further distance; and continue to displace the proximal end of the drive train with a force inputted to the proximal end of the drive train which varies so as to substantially maintain the second rate at which the motor is attempting to displace the proximal end of the drive train until the force inputted to the proximal end of the drive train is determined to exceed a threshold of the computed projected force.

2. The surgical stapling instrument of claim 1, wherein at least during displacement of the proximal end of the drive train, one or more of a distance displaced by the cutting edge or a force applied by the cutting edge to the grasped tissue, varies as compared with a distance displaced by the proximal end of the drive train or a force applied thereto by the motor.

3. The surgical stapling instrument of claim 2, wherein the variance depends on one or more properties of the grasped tissue and/or a degree of compliance of the drive train.

4. The surgical stapling instrument of claim 1, wherein the control circuit stops the displacement when the proximal end of the drive train has been displaced a maximum distance.

5. The surgical stapling instrument of claim 1, wherein the cutting edge is physically impeded from exceeding the first distance.

6. The surgical stapling instrument of claim 5, wherein the physical impediment is formed in the at least one jaw during manufacture after the cutting edge has been assembled with the at least one jaw.

7. The surgical stapling instrument of claim 5, wherein the physical impediment is characterized by a property which results in a distinguishable change in the monitored force inputted to the proximal end of the drive train to maintain the second rate when at least a portion of the cutting edge comes into contact with the physical impediment.

8. The surgical stapling instrument of claim 1, wherein the computation of the projected force comprises:

creation of an array of then current values of the monitored force and the corresponding position as the proximal end of the drive train is displaced over the fourth distance;

storage of the array in a memory buffer;

fit of one of a linear or best-fit curve to the stored array of monitored force and corresponding position values; and wherein the projected force is computed based on a projection of the fit linear or best-fit curve over one or more subsequent increments of displacement of the drive train.

9. The surgical stapling instrument of claim 1, wherein the computation of the projected force comprises:

as the proximal end of the drive train is displaced over the fourth distance, determine the then current values of the monitored force and corresponding position, compute a change in the monitored force over distance displaced and apply fuzzy logic to the current position and the change in the monitored force over distance displaced, wherein when the fuzzy logic returns a true value, the force inputted to the proximal end of the drive train is determined to exceed a threshold of the computed projected force.

10. The surgical stapling instrument of claim 1, wherein the surgical instrument comprises a handle and a shaft, a proximal end of the shaft being coupled with a distal end of the handle, the distal end of the shaft being coupled with the end effector, wherein the motor is located in the handle and the drive train is located in the shaft and extends from the proximal end of the shaft to the distal end of the shaft.

11. The surgical stapling instrument of claim 1, wherein the drive train comprises multiple linked components.

12. The surgical stapling instrument of claim 1, further comprising:

a handle comprising the motor and control circuit;

an articulation joint;

a shaft extending from a handle to the articulation joint to which the end effector is coupled, wherein the shaft comprises the drive train; and wherein the end effector comprises a firing beam operably coupled with the drive train and comprising the cutting edge; and wherein said articulation joint permits the end effector to be articulated and maintained in one or more directions relative to a longitudinal axis of the shaft via application of a holding force.

13. The surgical stapling instrument of claim 12, wherein the threshold of the computed projected force is less than the holding force.

14. The surgical stapling instrument of claim 1, wherein the surgical stapling instrument is configured to be attached and operated by a robot.

15. A control circuit for controlling a surgical instrument, the surgical instrument comprising an end effector configured to grasp tissue, the end effector comprising jaws comprising a cutting edge configured to be displaced a first distance from a proximal end to a distal end of the jaws such that at least a portion of the cutting edge transects tissue grasped by the end effector, the jaws further configured to receive a staple cartridge seatable in one of the jaws and including a sled and staples, the sled configured to be displaced a second distance from a proximal end to a distal end of the staple cartridge to deploy the staples into the tissue grasped by the end effector along the transection, the surgical instrument further comprising a motor located external to the end effector and a drive train operably coupled between the motor and the cutting edge and the sled, wherein the motor is configured to controllably displace a position of a proximal end of the drive train a controllable distance to displace the cutting edge and the sled so as to substantially simultaneously transect the tissue grasped by the end effector and deploy the staples therein along, and on either side of, the transection, the control circuit comprising:

a processor and a memory coupled therewith, the memory having stored therein computer readable instructions which, when executed by the processor, cause the processor to:

control a rate at which the motor is attempting to displace the proximal end of the drive train; and monitor during displacement of the proximal end of the drive train:

the position of the proximal end of the drive train; and a force inputted to the proximal end of the drive train by the motor; and during displacement of the proximal end of the drive train, cause the motor to:

displace the proximal end of the drive train a third distance, the third distance less than the first distance, with a force inputted to the proximal end of the drive train which varies so as to substantially maintain a first rate at which the motor is attempting to displace the proximal end of the drive train;

subsequent to displacing the third distance, continue to displace the proximal end of the drive train a fourth distance with a force inputted to the proximal end of the drive train which varies so as to substantially maintain a second rate at which the motor is attempting to displace the proximal end of the drive train, the second rate less than the first rate, during which the control circuit computes, based on the monitored force, a projected force which will be required to be inputted to the proximal end of the drive train so as to substantially maintain the second rate at which the motor is attempting to displace the proximal end of the drive train over a subsequent further distance; and continue to displace the proximal end of the drive train with a force inputted to the proximal end of the drive train which varies so as to substantially maintain the second rate at which the motor is attempting to displace the proximal end of the drive train until the force inputted to the proximal end of the drive train is determined to exceed a threshold of the computed projected force.

16. The control circuit of claim 15, wherein the computation of the projected force comprises:

creation of an array of then current values of the monitored force and the corresponding position as the proximal end of the drive train is displaced over the fourth distance;

storage of the array in a memory buffer;

fit of one of a linear or best-fit curve to the stored array of monitored force and corresponding position values; and wherein the projected force is computed based on a projection of the fit linear or best-fit curve over one or more subsequent increments of displacement of the drive train.

17. The control circuit of claim 15, wherein the computation of the projected force comprises:

as the proximal end of the drive train is displaced over the fourth distance, determine the then current values of the monitored force and corresponding position, compute a change in the monitored force over distance displaced and apply fuzzy logic to the current position and the change in the monitored force over distance displaced, wherein when the fuzzy logic returns a true value, the force inputted to the proximal end of the drive train is determined to exceed a threshold of the computed projected force.

18. The control circuit of claim 15, wherein the cutting edge is physically impeded from exceeding the first distance.

19. The control circuit of claim 18, wherein the physical impediment is formed in the at least one jaw during manufacture after the cutting edge has been assembled with the at least one jaw.

20. The control circuit of claim 18, wherein the physical impediment is characterized by a property which results in a distinguishable change in the monitored force inputted to the proximal end of the drive train to maintain the second rate when at least a portion of the cutting edge comes into contact with the physical impediment.

21. A method of operating a surgical instrument, the surgical instrument comprising an end effector configured to grasp tissue, the end effector comprising jaws comprising a cutting edge configured to be displaced a first distance from a proximal end to a distal end of the jaws such that at least a portion of the cutting edge transects tissue grasped by the end effector, the jaws further configured to receive a staple cartridge seatable in one of the jaws and including a sled and staples, the sled configured to be displaced a second distance from a proximal end to a distal end of the staple cartridge to deploy the staples into the tissue grasped by the end effector along the transection, the surgical instrument further comprising a motor located external to the end effector and a drive train operably coupled between the motor and the cutting edge and the sled, wherein the motor is configured to controllably displace a position of a proximal end of the drive train a controllable distance to displace the cutting edge and the sled so as to substantially simultaneously transect the tissue grasped by the end effector and deploy the staples therein along, and on either side of, the transection, the method comprising:

controlling a rate at which the motor is attempting to displace the proximal end of the drive train; and monitoring:

the position of the proximal end of the drive train; and a force inputted to the proximal end of the drive train by the motor; and during displacement of the proximal end of the drive train, causing the motor to:

displace the proximal end of the drive train a third distance, the third distance less than the first distance, with a force inputted to the proximal end of the drive train which varies so as to substantially maintain a first rate at which the motor is attempting to displace the proximal end of the drive train;

subsequent to attempting to displace the third distance, continue to displace the proximal end of the drive train a fourth distance with a force inputted to the proximal end of the drive train which varies so as to substantially maintain a second rate at which the motor is attempting to displace the proximal end of the drive train, the second rate less than the first rate, during which the control circuit computes, based on the monitored force, a projected force which will be required to be inputted to the proximal end of the drive train so as to substantially maintain the second rate at which the motor is attempting to displace the proximal end of the drive train over a subsequent further distance; and continue to displace the proximal end of the drive train with a force inputted to the proximal end of the drive train which varies so as to substantially maintain the second rate at which the motor is attempting to displace the proximal end of the drive train until the force inputted to the proximal end of the drive train is determined to exceed a threshold of the computed projected force.

22. The method of claim 21, wherein the computation of the projected force comprises:

creating an array of then current values of the monitored force and the corresponding position as the proximal end of the drive train is displaced over the fourth distance;

storing the array in a memory buffer;

fitting of one of a linear or best-fit curve to the stored array of monitored force and corresponding position values; and wherein the projected force is computed based on a projection of the fit linear or best-fit curve over one or more subsequent increments of displacement of the drive train.

23. The method of claim 21, wherein the computation of the projected force comprises:

as the proximal end of the drive train is displaced over the fourth distance, determining the then current values of the monitored force and corresponding position, computing a change in the monitored force over distance displaced and apply fuzzy logic to the current position and the change in the monitored force over distance displaced, wherein when the fuzzy logic returns a true value, the force inputted to the proximal end of the drive train is determined to exceed a threshold of the computed projected force.

24. The method of claim 23, further comprising forming the physical impediment in the at least one jaw during manufacture after the cutting edge has been assembled with the at least one jaw.

25. The method of claim 21, wherein the cutting edge is physically impeded from exceeding the first distance.

* * * * *